US005795570A

United States Patent [19]
Weber et al.

[11] Patent Number: 5,795,570
[45] Date of Patent: Aug. 18, 1998

[54] METHOD OF CONTAINING CORE MATERIAL IN MICROCAPSULES

[75] Inventors: Collin J. Weber, Atlanta, Ga.; Jennifer Ayres-Price, Mooresville, N.C.

[73] Assignee: Emory University, Atlanta, Ga.

[21] Appl. No.: 418,953

[22] Filed: Apr. 7, 1995

[51] Int. Cl.$^6$ .................... A61K 35/12; C12N 11/10; B01J 13/20

[52] U.S. Cl. .................. 424/93.7; 264/4; 264/4.3; 264/4.32; 424/424; 424/572; 428/402.2; 428/402.24; 435/178; 435/182; 435/325; 435/363; 435/366; 435/382

[58] Field of Search .................. 424/93.7, 424, 424/572; 435/174, 177, 178, 182, 240.22, 325, 363, 366, 382, 424, 572; 264/4, 4.3, 4.32; 428/402.2, 402.24

[56] References Cited

U.S. PATENT DOCUMENTS

| | | | |
|---|---|---|---|
| 4,352,883 | 10/1982 | Lim | 435/178 |
| 4,391,909 | 7/1983 | Lim | 435/178 |
| 5,084,350 | 1/1992 | Chang et al. | 428/402.2 |
| 5,227,298 | 7/1993 | Weber et al. | 435/178 |

OTHER PUBLICATIONS

Colton, C.K., et al. Bioengineering In Development Of The Hybrid Artificial Pancreas. Transactions of the ASME (1991) 113: 152–170.

de Vos, P., et al. Islets Protruding From Alginate–Polylysine Microcapsules Contribute To Bio-Incompatibility. Cell Transplantation (1994) 3: 106.

de Vos, P., et al. Possible Relationship Between Fibrotic Overgrowth Of Alginate–Polylysine–Alginate Microencapsulated Pancreatic Islets And The Microcapsule Integrity, Transplantation Proceedings (1994) 26: 782–783.

Goosen, M.F.A., et al. Optimization Of Microencapsulation Parameters: Semipermeable Microcapsules As A Bioartificial Pancreas. Biotechnology and Bioengineering (1985) 27:146–150.

Horsher, A., et al. Insulin Release From Different Models Of A Bioartificial Pancreas (Microencapsulation Versus Alginate–Coating). Transplantation Proceedings (1992) 24: 2950–2951.

Wong, H., et al. The Microencapsulation Of Cells Within Alginate Poly–L–Lysine Microcapsules Prepared With The Standard Single Step Drop Technique: Histologically Identified Membrane Imperfections And The Associated Graft Rejection. Biomat., Art. Cells & Immob. Biotech., (1991) 19(4), 675–697.

Zekron, T., et al. Alginate Coating Of Islets Of Langerhans: In Vitro Studies On A New Method For Microencapsulation For Immuno–Isolated Transplantation. Acta Diabetol (1992) 29: 41–45.

*Primary Examiner*—David M. Naff
*Attorney, Agent, or Firm*—John P. White; Cooper & Dunham LLP

[57] ABSTRACT

A core material such as animal tissue or cells is contained within a semipermeable vessel which may be a microcapsule, hollow fiber or plastic membrane having a semipermeable wall by a method that prevents the core material from incorporation into the wall of the vessel. This is accomplished by suspending the core material in a solution of polysaccharide gum such as an alkali metal alginate in an amount between about 0.2% and about 0.5%, removing and washing the core material to remove all but a thin layer of polysaccharide gum, and gelling the polysaccharide gum with multivalent cations or other means to form a pretreated core material. The pretreated core material is contained within a semipermeable vessel such as by suspending the pretreated core material in a solution of alkali metal alginate, forming the suspension into droplets, gelling the droplets to form temporary shape-retaining capsules and treating the capsules with a polymeric material having groups that react with and crosslink acid groups of the capsules to form a permanent semipermeable membrane around the capsules. A second permanent semipermeable membrane may be formed around the capsules to form double-walled microcapsules by further treating the capsules with the polymeric material. The semipermeable vessel may be impermeable to immune factors. Cells or tissue can be transplanted from a donor to a subject such as by using pancreatic islet tissue or cells as the core material of the double-walled microcapsules and transplanting the microcapsules by intraperitoneal injection into a diabetic subject.

25 Claims, 12 Drawing Sheets

"SINGLE-WALL"

"DOUBLE-WALL"

METHOD OF CONTAINING CORE MATERIAL IN MICROCAPSULES

The invention disclosed herein was made with Government support under NIH Grant No. R01DK39088 from the Department of Health and Human Services. Accordingly, the U.S. Government has certain rights in this invention.

Throughout this application, various references are referred to within parentheses. Disclosures of these references in their entireties are hereby incorporated by reference into this application to more fully describe the state of the art to which this invention pertains. Full bibliographic citation for these references may be found at the end of this application, preceding the claims.

BACKGROUND OF THE INVENTION

Pancreatic islet transplantation is a promising therapy for patients with insulin-dependent diabetes mellitus. Unfortunately, availability and yield of human islets are extremely limited, and allografts of human islets in immunosuppressed diabetic recipients have not been successful long-term (1). Treatment of large numbers of diabetic patients will almost certainly require the use of xenogeneic donor islets harvested from animals.

Techniques are currently available which allow isolation of islets from porcine, bovine, canine and rabbit donors (2–12). A major obstacle to clinical islet xenotransplantation is the lack of an effective immunosuppressive regimen, which will prevent cross-species islet graft destruction (1, 13–16, 60). Indefinite survival of islet xenografts has not been achieved except with the aid of porous mechanical barriers.

Since indefinite survival of a totally unrelated islet xenograft has not been achieved using immunologic manipulations, several investigators have examined the usefulness of porous membranes and envelopes as mechanical protective barriers against host immunocytes. The rationale for success with such interposed membranes is that cell—cell contact is required for cell-mediated cytotoxicity. In general, short-term islet xenograft function has been noted, with graft failure occurring as a result of an inflammatory response to the membrane material (7, 29, 75, 81).

A wide variety of intra and extravascular membrane devices have been tested; however, potential clinical complications, such as bleeding, coagulation, and bioincompatibility, mitigate against their use in diabetic patients (7, 9, 17–19, 29, 61, 81). One of the most promising islet immunoisolation methods is the poly-amino acid-alginate microcapsule. Donor islets are incorporated within tiny alginate spheres (300–800 microns in size) and are coated with a poly-amino acid, which provides a porous membrane. Intraperitoneal allografts and xenografts of rat, canine, porcine and human islets into streptozotocin diabetic rats and mice have promptly normalized blood glucose for up to 100 days (2–4, 6, 10, 11, 21–24, 26–29, 31, 32, 34, 35, 37, 38). Preliminary data have suggested correction of hyperglycemia by microencapsulated canine islet allografts (83), and porcine-to-monkey xenografts (89). Reduction of exogenous insulin requirements has also been reported following encapsulated islet allografts in at least one human patient (74).

Fasting hypoglycemia (asymptomatic) and abnormal glucose tolerance curves have been noted in rodent recipients with encapsulated islets grafts (2, 3, 25). However, multiple studies have documented excellent metabolic control following encapsulated islet transplants, compared to exogenous insulin therapy. Furthermore, the morbidity of microencapsulated islet grafts is significantly less than that of most other bioartificial pancreas designs and is significantly less than whole organ pancreatic grafting. The microcapsule design (multiple small spheres) is the optimal design for a porous membrane device, since this technique maximizes surface area-to-mass ratios and maximally reduces mass transfer resistances and diffusion time lags (7, 75). One disadvantage of microencapsulation of islets for treatment of diabetes appears to be that the peritoneal cavity is the only acceptable graft site, since microcapsules are both somewhat fragile and occupy a significant volume estimated approximately 200 cc of microcapsules for a human islet transplant of one-million islets, and that retrieval of all microcapsules may therefore be difficult, since they float freely within the peritoneal cavity and may become adherent to peritoneal surfaces if rejection or destruction occur. Nonetheless, the poly-amino acid-alginate microcapsule remains a useful means for islet xenografting.

Several laboratories have published data on microcapsules constructed with reagents other than the conventional alginate-polyamino acid technique. These include agarose, with or without polysterenesulfonic acid, hydroxyethyl methacrylate-methylmethacrylate (HEMA-MMA) and barium-alginate encapsulation or islet "coating" (30, 32, 33, 78–80). Bioincompatibility and limited islet graft survival have been observed.

Our standard method of microencapsulation was adapted from the previously published methods of Reach, et al. (20, 21). A complete description of our standard method of microencapsulation has been published on several occasions (2, 10, 23, 45, 55).

Briefly, isolated islets are suspended in from 1.85%–2.0% sodium alginate in saline and droplets containing islets in alginate are produced by extrusion through a 22 gauge air-jet needle. Droplets of alginate containing islets flow from a height of approximately 2 cm into a beaker containing 1.1% calcium chloride in saline. The negatively charged alginate droplets bind calcium and form a calcium alginate gel. The calcium alginate gel is temporary in that it may be solubilized under suitable conditions. Gelled droplets are decanted and subsequently incubated in calcium chloride for 10 minutes.

Thereafter, sequential washes with more dilute calcium chloride solutions are followed by a final wash in saline, after which 0.5 mg/ml poly-1-lysine is added and a subsequent incubation of 6 minutes allows for the positively charged poly-1-lysine to displace calcium ions and bind negatively charged alginate, producing a poly-electrolyte membrane. Initial studies utilized poly-1-lysine of 57,000 molecular weight. More recent studies have utilized smaller molecular weight poly-1-lysine (18–25,000 molecular weight). Following the poly-1-lysine incubation, microcapsules are washed in 0.1% CHES and a final 0.185%–0.2% solution of sodium alginate is added, forming a thin outer coating of sodium alginate. Finally capsulates are incubated in 55 mM sodium citrate, which solubizes any calcium alginate which has not reacted with poly-1-lysine. This method produces what has been termed a "single-wall" capsule.

With this technique, a greater than 100 day graft survival of Lewis rat islets, encapsulated and implanted into non-immunosuppressed, streptozotocin diabetic C57BLK and B10 mice has been noted (2, 3, 38). (See Table 1). Unfortunately, it has been found that identically encapsulated rat islets transplanted to spontaneously diabetic NOD mice (using the "single-wall" microcapsule technique) failed in 6–21 days, with a marked cellular reaction surrounding rejected microcapsules (2, 3). (See Table 1). Capsule breakage was also noted in biopsies of rejected grafts.

In an attempt to enhance the strength of the capsule wall, what has been termed the "double-wall" technique has been devised and published in detail (84, 45, 55). Basically, after completion of the "single-wall" method, but prior to the sodium citrate incubation, additional poly-1-lysine is added and a second incubation of about 6 minutes is followed by a subsequent wash in 0.1% CHES followed by an additional reincubation in dilute 0.185%–0.2% sodium alginate, followed by a final sodium citrate incubation. Islet xenografts with "double-wall" microencapsulation survive significantly longer in NOD mice (p<0.01) (see table 1), and "double-wall" capsules have greater integrity (55).

There are no long-term studies of encapsulated pancreatic islet isografts, and, therefore, the limits of durability and functional graft survival of microencapsulated islets are largely unknown. Almost all experiments analyzing the function of encapsulated islet grafts have relied on either mouse or rat recipients, and graft function has been monitored for greater than 200 days in few studies (2, 3, 6, 34, 36). Because of the dramatic enhancement of islet allo- and xenograft survival by microencapsulation compared to non-encapsulated grafts, relatively little attention has been focused on the long-term limits of encapsulated islet graft survival. This is extremely relevant to clinical application of the microcapsule method, since a transplant technique which fails after less than one year of function might be considered clinically unacceptable.

Careful reading of several reports on microencapsulated islet allo- and xenografts in rodents reveals that indefinite graft survival rarely occurs. In fact, capsule attrition is noted in graft biopsies even in successful recipients. Capsule breakage and fibrous reactions to broken capsules are focally present in most biopsies of functioning transplants as well. There is general agreement that capsule attrition is a significant problem which must be circumvented if the microcapsule technique is applied to man. The recent report by Horcher (82) that rat islet isografts in microcapsules remained intact, functional, and without reaction for greater than 8 weeks, suggests that capsule attrition may be minimized if allo- and xeno-reactivity to encapsulated islets can be abolished.

A second problem with microencapsulated islet grafting is the recent observation that mice and rats with spontaneous, as opposed to induced, diabetes (BB rats and NOD mice) destroy encapsulated islet allografts and xenografts in spite of the porous microcapsule barrier (2, 3, 10–12, 22, 24, 31, 37, 38, 43, 44, 55). Accelerated destruction of encapsulated islets by NOD mice and BB rats as compared to streptozotocin diabetic recipients is considered an obstacle to use of encapsulated islet grafts in insulin-dependent diabetic patients and has led several experimental groups to suggest that anti-islet autoimmunity may be involved in the destruction of encapsulated grafts by NOD mice and BB rats. Effector mechanisms of islet graft destruction in these models has been a subject of intense study in our laboratory. It has been suggested that microcapsules protect donor islets from host destruction in part by prohibiting cell-cell contact with host immunocytes (7). It is well documented that T-lymphocytes are involved in destruction of non-encapsulated islet xenografts (8, 13, 39–42, 62). While both CD4+ and CD8+ T cells are involved in allograft reactions, CD4+ T cells are predominately involved in xenogenic reactions (2, 56–60, 62, 65). In mice, it has been shown that CD4+ helper T cells recognize xeno-antigens as nominal antigens when presented by a host antigen presenting cell, rather than directly as in alloantigen recognition (15, 43, 55). In addition, however, it has been documented that complement and cytokines are crucial to xenograft destruction (7, 14–16, 39). It has been reported that conventionally designed poly-1-lysine alginate microcapsules prevent islets from coming in contact with host antibodies.

It remains unclear why mice with spontaneous diabetes (NOD mice) aggressively destroy encapsulated islets while mice with induced diabetes (streptozotocin mediated) do not. There is some evidence that NOD mice respond to foreign antigens more aggressively than do other strains of mice (66). Several groups have suggested that destruction of donor islets, even within microcapsules, may be a recapitulation of autoimmune destruction of host islets by NOD mice. Cytotoxic T cells and antibodies specific for islet beta cells have been identified, characterized, and cloned from NOD mice (49–54, 64). Although NOD diabetes is widely assumed to be antigen driven, no one peptide has been implicated (67). Recent studies have indicated that loss of tolerance to islet antigens in NODs correlates with the appearance of a Th1 immune response to an important islet antigen, glutamic acid decarboxylase (72, 85). By analogy to transplant and other autoimmune reactions, it has been suggested that helper T cells function to activate CD8+ cells, which damage beta cells by direct cytotoxic attack. In addition, however, some recent studies have also suggested that beta cell killing by NODs may be indirect, from a non-specific inflammatory response which initially involves CD4+ cells but primarily includes infiltrating macrophages, which release cytokines and oxygen-free radicals, well-known beta cell toxins (46–48, 63).

Colton (7, 75) summarized a working hypothesis for possible pathways of rejection of immunoisolated islets, which includes release or secretion of some donor protein or cell surface or cytoplasmic antigen(s) through the membrane, where recognition, processing and presentation by host antigen presenting cells to host T cells results in activation of macrophages, cytotoxic T cells. In addition, activated B cells release specific antibodies and complement cytokines accumulate in the local milieu surrounding microcapsules.

Recently, deVos, et al. (77), have reported that incomplete encapsulation of donor islets and/or actual protrusion of donor islets through the poly-1-lysine alginate membrane may contribute to capsule breakage and focus immune responses to damaged or imperfect capsules. This concept is quite intriguing, since it is not accounted for by the Colton model of released or secreted antigen traversing an intact porous membrane. We have obtained results quite similar to those reported by deVos and believe that this is a critical issue in poly-1-lysine alginate microcapsule design which must be corrected.

As described herein, we have discovered that the entrapment of donor islets within the microcapsule wall contributes to the aforementioned problems with microencapsulation. We demonstrate that such entrapment provokes host cellular reactions to defective microcapsules, increases microcapsule fragility, decreases microcapsule durability, and results in limited survival of the graft. Although not wishing to be bound by any particular theory, it is believed that peripheral positioning of islets within alginate spheres during the microencapsulation process may be due to sheer forces, centrifugal forces, and/or deceleration forces.

SUMMARY OF THE INVENTION

This invention provides a method of pretreating viable tissue or cells to be contained within a semipermeable vessel which comprises: (a) suspending the viable tissue or cells in a solution comprising a substance capable of forming a gel, wherein the solution is physiologically compatible with the viable tissue or cells; and (b) treating the resulting suspension under conditions permitting the substance to form a gel, so as to thereby pretreat the viable tissue or cells to be contained within a semipermeable vessel.

This invention also provides a method of containing viable tissue or cells within a semipermeable vessel which comprises: (a) pretreating the viable tissue or cells according to the aforementioned method so as to obtain pretreated viable tissue or cells; and (b) forming a semipermeable vessel around the pretreated viable tissue or cells, so as to thereby contain the viable tissue or cells within a semipermeable vessel.

This invention also provides a method of transplanting viable tissue or cells from a donor to a subject which comprises: (a) containing the viable tissue or cells from the donor within a semipermeable vessel according to the aforementioned method; and (b) transplanting into the subject the resulting contained viable tissue or cells, thereby transplanting the viable tissue or cells from the donor to the subject.

This invention further provides a method of transplanting viable tissue or cells from a donor to a subject so as to protect the viable tissue or cells from destruction by the subject's immune system which comprises: (a) containing the viable tissue or cells from the donor within a semipermeable vessel, said semipermeable vessel being impermeable to immune factors, according to the aforementioned method of containing viable tissue cells within a semipermeable vessel; and (b) transplanting into the subject the resulting contained viable tissue or cells, thereby transplanting the viable tissue or cells from the donor to the subject.

This invention also provides a method of treating a subject suffering from diabetes which comprises transplanting an amount of viable pancreatic islets from a donor to the subject according to the aforementioned method of transplanting viable tissue or cells from a donor to a subject so as to protect the viable tissue or cells from destruction by the subject's immune system, wherein the amount of viable pancreatic islets transplanted is an amount effective to treat diabetes.

This invention also provides viable tissue or cells pretreated according to the aforementioned method of pretreating viable tissue or cells.

This invention further provides viable tissue or cells contained within a semipermeable vessel according to the aforementioned method of containing viable tissue or cells within a semipermeable vessel.

Finally, this invention provides viable tissue or cells contained within a semipermeable vessel according to the aforementioned method, wherein the semipermeable vessel is a microcapsule.

BRIEF DESCRIPTION OF THE FIGURES

FIG. 7A: Islet embedded in "double-wall", alginate microcapsule; phase contrast. FIG. 7B: Islet in wall at rejection, by recipient diabetic NOD mouse.

DETAILED DESCRIPTION OF THE INVENTION

Figure 1:
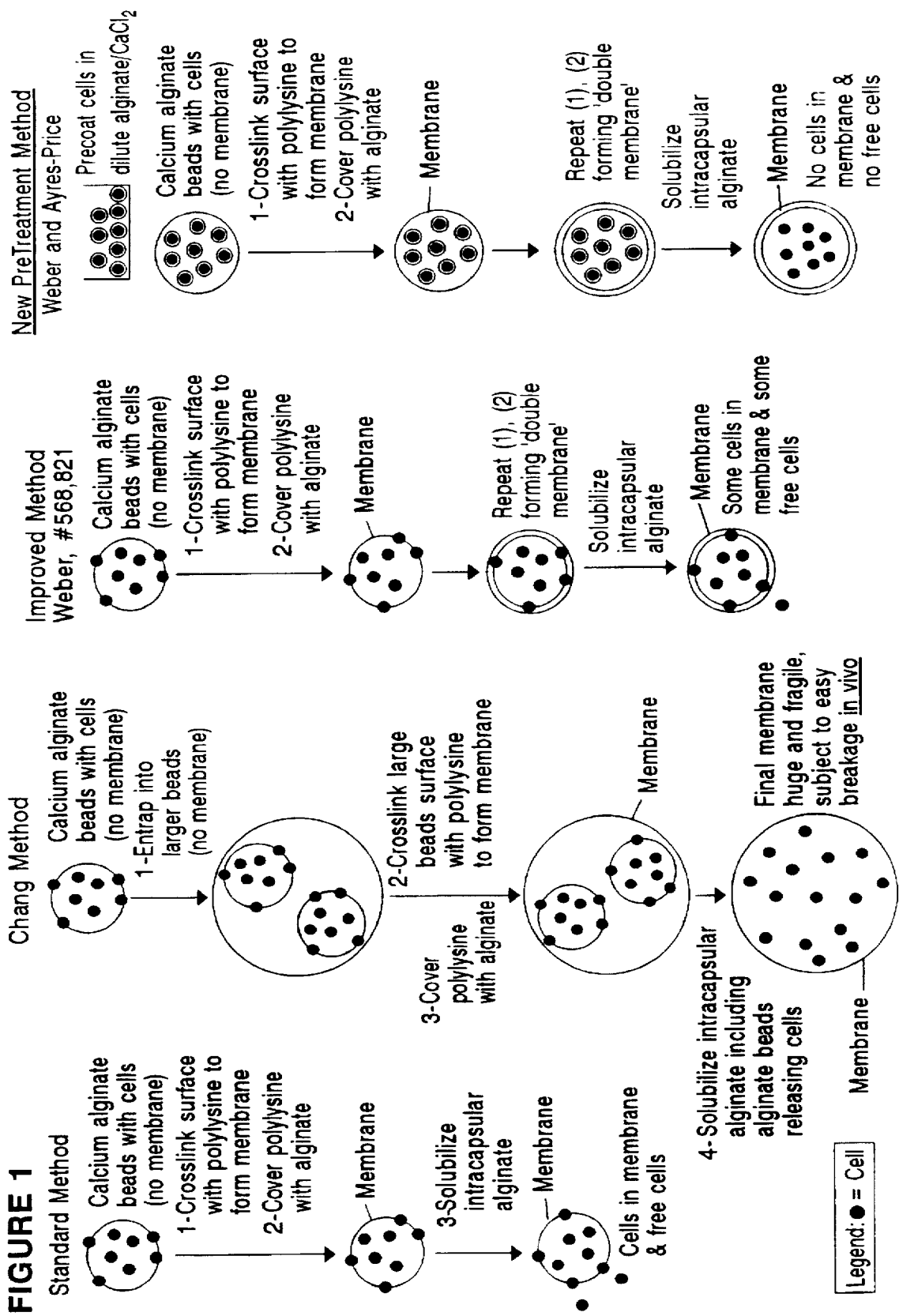
FIG. 1: "Single-wall" and "double-wall" methods of microencapsulation, compared to the new pretreatment method of the subject invention.
Figure 2:
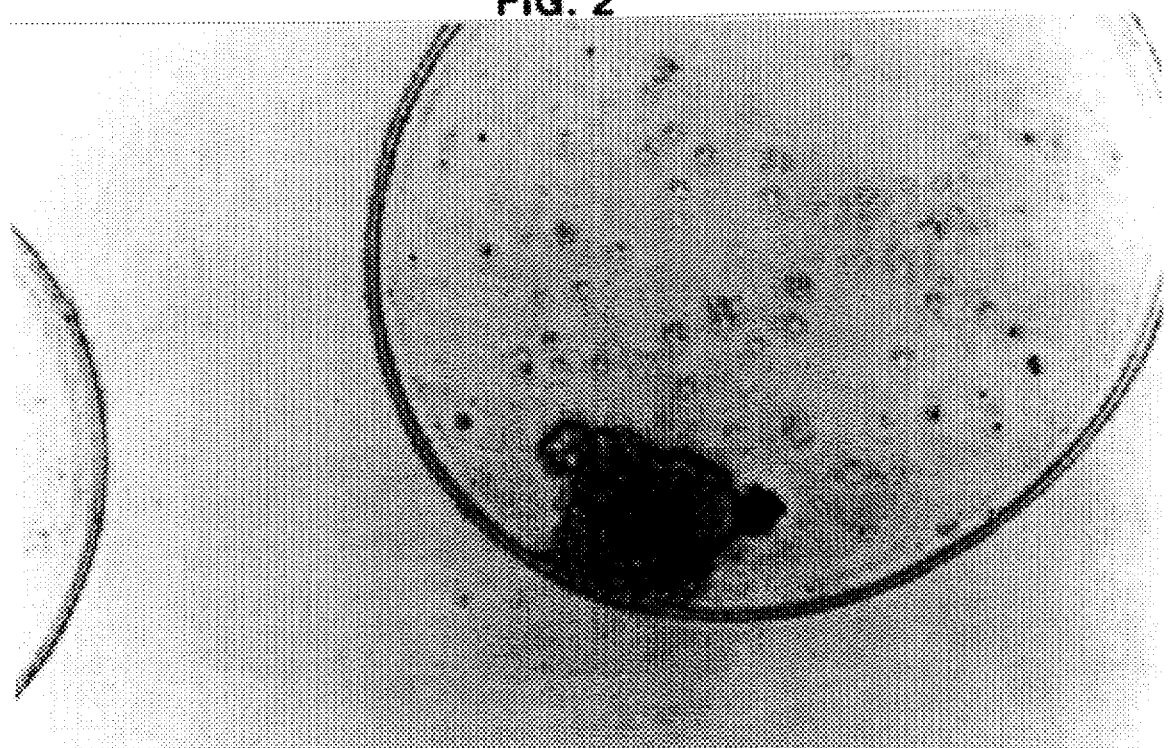
FIG. 2: Phase microscopic view of non-pretreated, "double-wall" method showing islet embedded in microcapsule wall.
Figure 3:
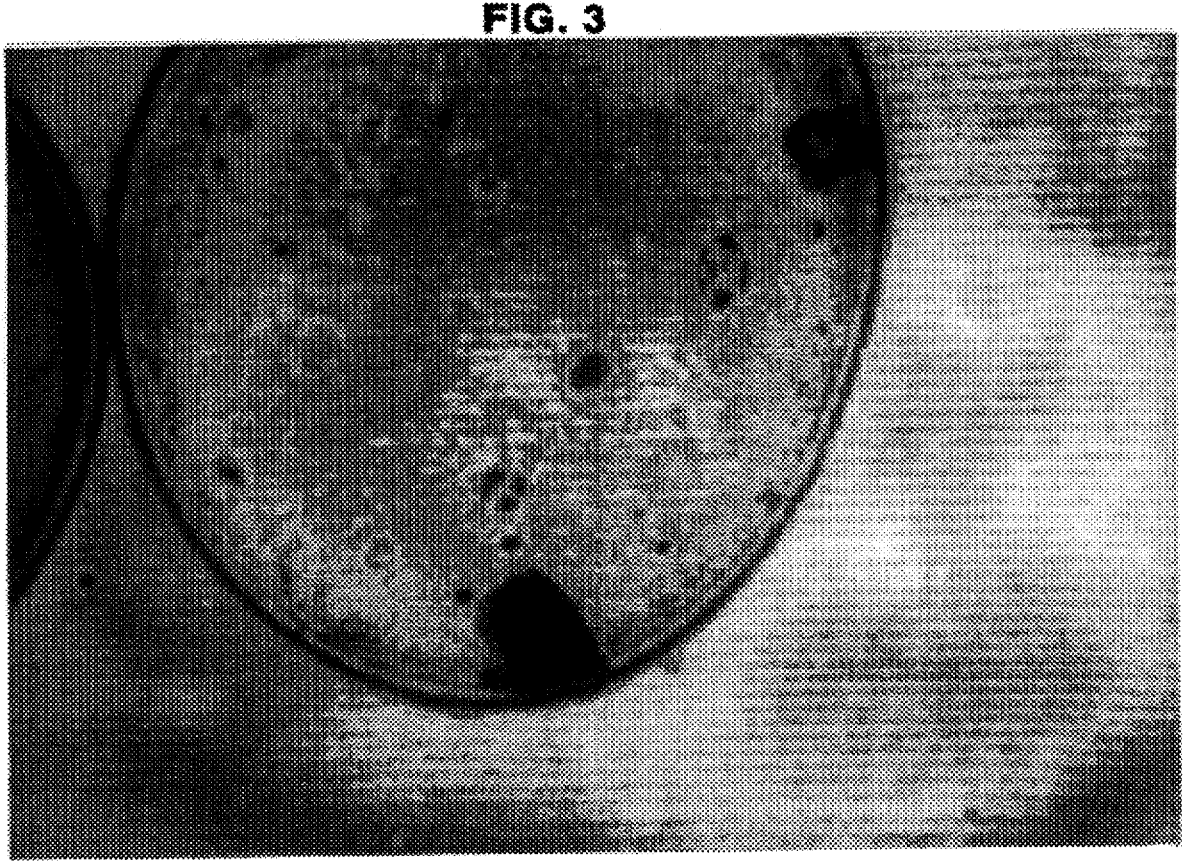
FIG. 3: Confocal microscopy, showing islet embedded in a non-pretreated "double-walled" microcapsule wall.
Figure 4:
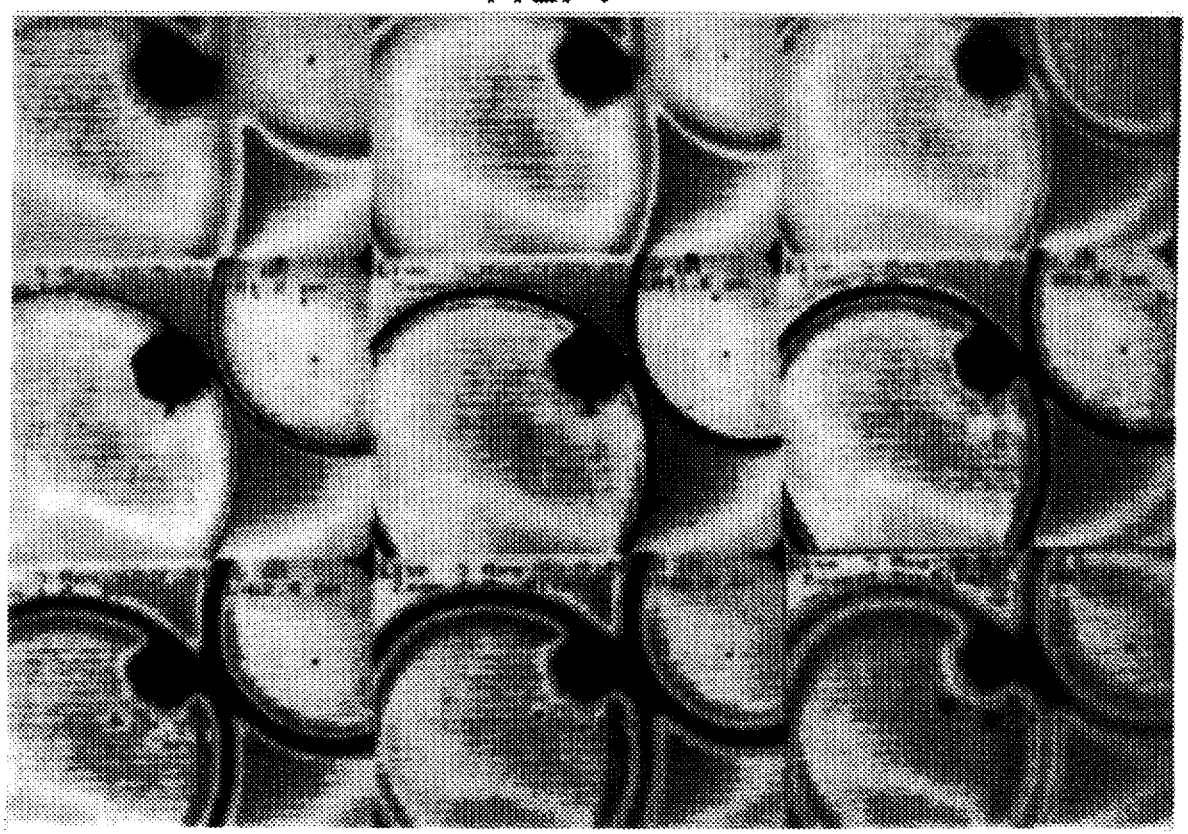
FIG. 4: Same as FIG. 3; sequential-depth confocal images, showing (center image) that when capsule wall is in focus, an islet is found to be embedded in capsule wall.

This invention provides a method of pretreating a core material to be contained within a semipermeable vessel which comprises: (a) suspending the core material in a solution comprising a "pretreatment substance", i.e. a substance capable of forming a gel; and (b) treating the resulting suspension under conditions permitting the pretreatment substance to form a gel, so as to thereby pretreat the core material to be contained within a semipermeable vessel.

As used herein, the term "core material" indicates any material which is intended to be contained within a semipermeable vessel for subsequent transplantation into an organism. Core material includes, but is not limited to, macromolecules, such as enzymes or immunoproteins; viable tissue; and viable cells. The subject invention is particularly applicable to viable tissue and cells. Accordingly, in one embodiment, the subject invention provides a method of pretreating viable tissue or cells to be contained within a semipermeable vessel which comprises: (a) suspending the viable tissue or cells in a solution comprising a substance capable of forming a gel, said solution being physiologically compatible with the viable tissue or cells; and (b) treating the resulting suspension under conditions permitting the substance to form a gel, so as to thereby pretreat the viable tissue or cells to be contained within a semipermeable vessel.

The term "semipermeable vessel" as used herein is meant to indicate any means capable of containing a core material, which means prevents at least some contact between the core material contained within the semipermeable vessel and the environment outside. If the core material comprises viable tissue or cells, the semipermeable vessel may be formed so as to prohibit the viable tissue or cells from escaping and to only permit a particular substance secreted by the viable tissue or cells to permeate. The semipermeable vessel may also be formed so as to only selectively permit particular substances from the environment to enter. Such semipermeable vessels for containing core material are well known in the art. A semipermeable vessel for purposes of the subject invention may be either an intravascular device or an extravascular device. Moreover, for purposes of the subject invention, a semipermeable vessel may be in any geometric form, including, but not limited to, planar forms; tubular forms, such as hollow fibers; or spherical forms, such as microcapsules.

A "physiologically compatible" solution as used herein is any solution in which viable tissue or cells remain viable, and such solutions are well known to those of ordinary skill in the art.

The semipermeable vessel of the subject invention may be formed by any method known in the art for forming semipermeable vessels. When the semipermeable vessel is a microcapsule, it is generally formed by suspending the pretreated core material in a solution comprising an "encapsulating material", i.e. a material which is capable of forming a gel; forming the resulting suspension into droplets of a size sufficient to encapsulate the core material; treating the resulting droplets under conditions permitting the encapsulating material to form a gel so as to form temporary shape-retaining capsules; and forming a permanent semipermeable membrane around the resulting temporary shape-retaining capsules.

The pretreatment substance in the aforementioned method may be either the same as or different than the encapsulating material. Substances and materials capable of forming a gel and hence useful for purposes of either the pretreatment substance or the encapsulating material in the subject invention are well known in the art and include, but are not limited to, natural or synthetic polysaccharide gums which gel upon a change in conditions such as a change in pH or exposure to multivalent ions. Gums useful in the subject invention may also comprise groups which react with constituents of polymers to cause crosslinking of the polymers to thus form a permanent semipermeable membrane. When the gum used as the pretreatment substance is the same as the gum used as the encapsulating material, it is preferred that the gum comprise such groups which react with polymeric constituents. Examples of polysaccharide gums capable of forming a gel include but are not limited to, alkali metal alginates, such as sodium alginate; guar gum; gum arabic; carrageenan; pectin; tragacanth gum; xanthan gum; and any acidic fraction of any of the aforementioned gums. Examples of groups which react with polymeric constituents to crosslink the constituents and form a permanent semipermeable membrane include, but are not limited to, acid groups. Therefore, in one embodiment of the aforementioned method of the subject invention, especially when the gum used as the pretreatment substance is the same as that used as the encapsulating material, the substance capable of forming a gel is a gum which comprises acid groups, for example an alkali metal alginate.

When the pretreatment substance is an alkali metal alginate, in one embodiment the final concentration of the alkali metal alginate in the suspension prior to treating the suspension so as to cause the pretreatment substance to gel is between about 0% and about 2%. In another embodiment, the final concentration of the alkali metal alginate in the suspension prior to treating the suspension is between about 0% and about 1%. In another embodiment, the final concentration of the alkali metal alginate in the suspension prior to treating the suspension is between about 0% and about 0.5%. In still another embodiment, the final concentration of the alkali metal alginate in the suspension prior to treating the suspension is about 0.2%.

Conditions which permit the pretreatment substance to form a gel in the method of the subject invention are well known in the art and depend on the specific substance which is used to pretreat the core material. In general, such substances gel upon a change in pH or upon reacting with multivalent ions. For example, if the pretreatment substance is an alkali metal alginate, such as sodium alginate, conditions permitting the substance to gel include exposing the substance to a solution of multivalent cations, including, but not limited to, calcium cations. Other multivalent cations, such as barium or magnesium, may be used, however, calcium is preferred since it is physiologically compatible with most viable tissue or cells. Accordingly, in one embodiment of the method for pretreating a core material of the subject invention wherein the core material is suspended in a solution comprising an alkali metal alginate, treating the suspension in step (b) comprises contacting the suspension with a solution comprising multivalent cations. In one embodiment when the treating comprises contacting the suspension with a solution comprising multivalent cations, the multivalent cations are calcium cations.

Pretreating viable tissue or cells according to the method of the subject invention overcomes several obstacles to containing viable tissue or cells within a semipermeable vessel. Viable tissue or cells, including individual viable cells, pretreated according to the subject method are prevented from becoming lodged within the wall of a semipermeable vessel, the lodging possibly being the result of centrifugal, sheer, deceleration, or electrostatic forces which arise during the process of vessel formation. The subject method therefore makes it possible to contain previously-uncontainable single viable cells within a semipermeable vessel. In general, it is advantageous to contain core material within a semipermeable vessel prior to transplanting such material to an organism, since vessels are relatively easy to separate from the organism's tissue and/or circulation, and materials contained therein are thus more easy to retrieve from the organism than transplanted uncontained materials.

Where xenogenic material is transplanted, or for that matter any material which would elicit any sort of immune response in the organism, another advantage to containing materials within semipermeable vessels prior to transplantation is that the vessels prevent host immune cells and host antibodies from contacting and destroying the materials. Also, by preventing viable tissue or cells from being lodged within the wall of a semipermeable vessel in which they are contained, the subject method increases the structural durability and consequently the life-span of transplanted semipermeable vessels. Finally, if the tissue or cells are not lodged within the vessel walls, they do not come into contact with the environment outside of the vessel. Therefore, the subject method increases the biocompatability of semipermeable vessels containing viable tissue or cells which are immunogenic to a subject into which they are transplanted.

This invention also provides a method of containing a core material within a semipermeable vessel which comprises: (a) pretreating the core material according to the aforementioned method so as to obtain pretreated core material; and (b) forming a semipermeable vessel around the pretreated core material, so as to thereby contain the core material a semipermeable vessel. In one embodiment, the core material comprises viable tissue or cells.

In the subject method of containing a core material, the core material may be contained within any type of semipermeable vessel. Such semipermeable vessels are well known in the art as described above and include, but are not limited to, hollow fibers, plastic membranes, and microcapsules. In one embodiment of the aforementioned method, the semipermeable vessel is a microcapsule.

When the semipermeable vessel is a microcapsule, it generally is formed as described above, i.e. by suspending the pretreated core material in a solution comprising an encapsulating material and, if the core material comprises viable tissue or cells, a solution which is physiologically compatible with the viable tissue or cells; forming the resulting suspension into droplets of a size sufficient to encapsulate the core material; treating the resulting droplets under conditions permitting the encapsulating material to form a gel so as to form temporary shape-retaining capsules; and forming a permanent semipermeable membrane around the resulting temporary shape-retaining capsules.

In the formation of microcapsules, after the core material has been suspended in the encapsulating material, any means sufficient to form the suspension into droplet may be used. For example, the suspension may be extruded through a means, such as an air-jet needle, having an exit in a shape which causes the suspension to take on the shape of droplets. Other examples of means sufficient to form suspensions into droplets are well known to those of ordinary skill in the art and include, but are not limited to, dispersing the suspension by means of a spraying device, or blowing air across the suspension.

After droplets are formed in the aforementioned method, they are treated under conditions permitting the encapsulating material to gel. Such conditions are well known in the art as described above. In one embodiment wherein the encapsulating material is an alkali metal alginate such as sodium alginate, the droplets are contacted with a solution which comprises multivalent cations, for example by permitting the droplets to fall or flow into such a solution. In one embodiment when the droplets are contacted with a solution which comprises multivalent cations, the multivalent cations are calcium cations. Treating the droplets under conditions permitting the encapsulating material to form a gel causes the droplets to form into temporary shape-retaining capsules. These temporary shape-retaining capsules may be reliquified by reversing the conditions which permitted the material to form a gel.

In the formation of microcapsules in the method of the subject invention, after the droplets are formed into temporary shape-retaining capsules, a permanent, semipermeable membrane is formed therearaound. Generally, the permanent semipermeable membrane is formed by contacting the temporary shape-retaining capsules with a substance comprising polymeric constituents which react with groups on the encapsulating material and consequently crosslink to form a membrane. In one embodiment when the material comprises acid groups, forming the permanent semipermeable membrane comprises contacting the temporary shape-retaining capsules with a substance comprising polymeric constituents, such as amine or imine groups, which react with acid groups. In one embodiment when the temporary shape-retaining capsules are contacted with a substance comprising constituents which react with acid groups, the substance is a polyamino acid, for example poly-1-lysine.

Formation of microcapsules as described above is well known to those of ordinary skill in the art and is further described in U.S. Pat. No. 5,227,298, Weber et al., issued Jul. 13, 1993, which is hereby incorporated by reference.

In another embodiment of the method of the subject invention, a microcapsule containing a pretreated core material according to the subject method is further treated so as to form a second permanent semipermeable membrane therearound, resulting in a "double walled" microcapsule. The formation of "double walled" microcapsules is known in the art and is described in U.S. Pat. No. 5,227,298.

The permeability of the semipermeable vessel of the subject invention may be varied by means known to those of ordinary is skill in the art. Permeability may be selected based on factors known in the art, including, but not limited to, the size of the core material to be contained; if the core material comprises viable tissue or cells, the size of any substances which are required by the viable tissue or cells to remain viable and therefore are required to penetrate the semipermeable vessel; the size of any biologically-active substances secreted by contained viable tissue or cells and which are intended to pass through the semipermeable vessel; and the immunogenicity of core material. For example, albumin, the molecular weight of which is approximately 68,000, may be required by some cells in order to remain viable. Accordingly, a semipermeable vessel containing such cells should be at least permeable to substances having a molecular weight of approximately 68,000. As another example, biologically-active substances secreted by viable tissues or cells are typically from about 5000 to about 6000 molecular weight. Therefore, semipermeable vessels containing tissue or cells which secrete such a biologically-active substance should be at least permeable to substances having a molecular weight of about 5000 to about 6000 if it is desired that the biologically-active substance penetrate the vessel. As used herein, a biologically-active substance is any substance which elicits an effect within an organism, for example insulin. As a further example, if the core material is likely to elicit an immune response in a subject into which it is transplanted, it would be desirable that the semipermeable vessel be made impermeable to immune factors. As used herein, an immune factor is any cell or substance which is produced by an animal in response to an immunogen in order to destroy substances which possess that immunogen. Examples of immune factors include, but are not limited to, immunocytes, such as T-lymphocytes; immunoglobulin; and complement protein. The size of the smallest known immune factor, IgG, is approximately 160,000 molecular weight. Therefore, a semipermeable vessel which is impermeable to substances of approximately 160,000 molecular weight will be sufficient to be impermeable to immune factors. The term "immunogen" indicates any substance, for example an antigen, or a specific epitope on an antigen, which elicits an immune response in a subject.

In one embodiment of the method of the subject invention of containing viable tissue or cells within a semipermeable vessel, the viable tissue or cells are mammalian.

In another embodiment of the method, the viable tissue or cells comprise viable tissue or cells which are known to secrete a biologically-active substance. Biologically-active substances are known to those of ordinary skill in the art and include, but are not limited to, hormones; neurotransmitters; and factors which are required for biological functions, such as growth stimulating factors, blood coagulating factors, and immune-stimulating factors. Viable tissue or cells may secrete a biologically-active substance naturally, i.e. in their native state, or they may be genetically engineered to secrete a biologically active substance. The biologically-active substance may be a substance whose site or sites of action are relatively proximal to the location at which it is secreted, or it may be a humoral substance, i.e. a substance whose site or sites of action are relatively distant from the location at which it is secreted, which substance reaches said site or sites of action via the circulatory system of the organism.

When the viable tissue or cells secret a biologically-active substance, in one embodiment they are endocrine tissue or cells. Endocrine tissue and cells are known to those of ordinary skill in the art and include, but are not limited to, pancreatic islets, hepatocytes, parathyroid cells, or pituitary cells.

In another embodiment wherein the viable tissue or cells secrete a biologically-active substance, the viable tissue or cells are neuroectodermal cell. Examples of neuroectodermal cells include, but are not limited to, adrenal cells and lymphocytes.

This invention also provides a method of transplanting viable tissue or cells from a donor to a subject which comprises: (a) containing the viable tissue or cells from the donor within a semipermeable vessel according to the aforementioned method; and (b) transplanting into the subject the resulting contained viable tissue or cells, thereby transplanting the viable tissue or cells from the donor to the subject.

Any transplantation method may be used in the method of the subject invention to transplant the contained viable tissue or cells in step (b), and such methods are well known to those of ordinary skill in the art. Examples of methods by which the contained viable tissue or cells may be transplanted include, but are not limited to, injecting the contained viable tissue or cells into the subject or surgically implanting the contained viable tissue or cells into the subject. When the viable tissue or cells are introduced into the subject by injection, the injection may be subcutaneous, intraperitoneal, intramuscular, or intravenous injection.

The contained viable tissue or cells may be transplanted into any site within the subject. The site where the contained viable tissue or cells are transplanted may be determined based on factors known to those of ordinary skill in the art. Such factors include, but are not limited to, the quantity of the semipermeable vessels to be transplanted into the subject, the fragility of the semipermeable vessels to be transplanted, and, if the contained viable tissue or cells secrete a biologically-active substance which is intended to affect the subject, whether the substance secreted by the viable tissue or cells is a humoral substance or whether it is a substance which must be relatively proximal to a particular site within the subject in order to elicit its intended affect. If a relatively large quantity of semipermeable vessels is to be transplanted into the subject, then such amount may be effectively transplanted into the peritoneum of the subject. Otherwise, any site within the subject where the amount of internal pressure is insufficient to damage the transplanted semipermeable vessels may be chosen. For example, a transplant site may be a site where fatty tissue is present, such as, if the subject is a human, the thigh or the armpit.

In one embodiment of the aforementioned method for transplanting viable tissue or cells from a donor to a subject, the viable tissue or cells comprise viable tissue or cells which are known to secrete a biologically-active substance and which substance is intended to affect the subject. Viable tissue or cells known to secrete a biologically-active substance are known in the art as described above. In one embodiment of the aforementioned method wherein the viable tissue or cell are known to secrete a biologically-active substance, the viable tissue or cells are endocrine tissue or cells. Endocrine tissue and cells are known to those of ordinary skill in the art as described above. In another embodiment of the aforementioned method wherein the viable tissue or cells are known to secrete a biologically-active substance, the viable tissue or cells are neuroectodermal tissue or cells. Neuroectodermal tissue and cells are known to those of ordinary skill in the art as described above.

Viable tissue or cells may be transplanted to subjects afflicted with various disorders according to the method of the subject invention in order to treat such subjects. For example, hepatocytes may be transplanted into a hemophiliac to deliver blood coagulation factors. Pancreatic islets may be transplanted to a diabetic subject according to the subject method to regulate blood glucose levels. Cells transfected with a gene engineered to express a particular protein, such as growth hormone, may be transplanted to a subject suffering from a deficiency in the protein according to the subject method. Cloned cells predetermined to secrete granulocyte macrophage-stimulating factor may be transplanted to a subject being treated by chemotherapy according to the subject method so as to permit more chemotherapeutic drugs to be administered to the subject without increasing the adverse side-effects associated with the drugs.

The subject invention is furthermore useful for treating a subject afflicted with a tumor. For example, cells preselected for secretion of gamma-interferon may be transplanted to a subject afflicted with a tumor in order to inhibit the growth of the tumor. Also, tumor cells may be removed from a subject afflicted with a tumor, transfected with a gene expressing a growth factor, such as cytokine, and subsequently transplanted back into the subject according to the method of the subject invention to elicit an immune response in the subject to the cells of the tumor.

A subject suffering from a deficiency in a certain hormone may be treated according to the subject method. For example, adrenal tissue or cells may be transplanted to a subject having a deficiency in cortisone. Likewise, parathyroid tissue or cells may be transplanted to a subject suffering from a thyroid deficiency. Pituitary tissue or cells, secreting hormones such as luteinizing hormone or follicle stimulating hormone, may be transplanted to a subject according to the subject method in order to treat infertility in the subject or in order to decrease adverse side-effects associated with menopause.

Furthermore, brain tissue or cells secreting neurotransmitters may be useful for treating certain disorders, such as schizophrenia, if transplanted according to the method of the subject invention. As another example, tissue or cells which secrete endorphins may be transplanted in order to relieve pain in a subject suffering therefrom.

The subject in the method of the subject invention may be any subject. In one embodiment, the subject is a mammal. In a further embodiment, the subject is a human.

This invention further provides a method of transplanting viable tissue or cells from a donor to a subject so as to protect the viable tissue or cells from destruction by the subject's immune system which comprises: (a) containing the viable tissue or cells from the donor within a semipermeable vessel, which semipermeable vessel is impermeable to immune factors, according to the subject method of containing viable tissue of cells within a semipermeable vessel; and (b) transplanting into the subject the resulting contained viable tissue or cells, thereby transplanting the viable tissue or cells from the donor to the subject.

In one embodiment of the method of the subject invention of transplanting viable tissue or cells from a donor to a subject so as to protect the viable tissue or cells from destruction by the subject's immune system, the subject is a mammal, for example a human. In the method of the subject invention wherein the viable tissue or cells are protected from destruction by the subject's immune system, the donor and the subject may be different species. Alternatively, the donor and the subject may be the same or a similar species. In one embodiment of the method of the subject invention, the donor and the subject are both mammals. In one embodiment when the donor and the subject are both mammals, the subject is a human being.

Any viable tissue or cells may be transplanted from the donor to the subject in the subject method of transplanting viable tissue or cells from a donor to a subject so as to protect the viable tissue or cells from destruction by the subject's immune system. In one embodiment, the viable tissue or cells comprise pancreatic islets.

Accordingly, this invention also provides a method of treating a subject suffering from diabetes which comprises transplanting an amount of viable pancreatic islets from a donor to the subject according to the subject method of transplanting viable tissue or cells from a donor to a subject so as to protect the viable tissue or cells from destruction by the subject's immune system, wherein the amount of viable pancreatic islets transplanted is an amount effective to treat diabetes.

The amount of viable pancreatic islets effective to treat diabetes in the method of the subject invention is determined based on factors known to those of ordinary skill in the art. Such factors include, but are not limited to, the size of the subject being treated and the quantity of insulin produced by each transplanted islet.

This invention also provides viable tissue or cells pretreated according to the subject method of pretreating viable tissue or cells. This invention further provides viable tissue or cells contained within a semipermeable vessel, including viable tissue or cells contained within a microcapsule, according to the subject method of containing viable tissue or cells within a semipermeable vessel.

This invention will be better understood from the "Experimental Details" section which follows. However, one skilled in the art will readily appreciate that the specific methods and results discussed therein are not intended to limit, but rather to merely illustrate, the invention as described more fully in the claims which follow thereafter.

Experimental Details

We compared the survival rate in mice of transplanted single-wall and double-wall microcapsules containing islets which had been pretreated according to the method of the subject invention to unpretreated microencapsulated islets. Islets were obtained from a variety of donor species, including rat, rabbit, calf, dog, and human.

Islet Pretreatment

Islets were washed in Hank's balanced salt solution and allowed to settle. Excess Hank's solution was removed, leaving a pellet of islets in approximately 0.2 cc of Hank's solution. Thereafter, 1.5 ml of a 2.0% solution of sodium alginate in 13.5 ml of sodium chloride were added to produce a final concentration 0.2% alginate. Islets were rotated in this liquid for 10 minutes. Thereafter, they were centrifuged at 2000 RPM for 3 minutes, supernatant was removed, the cells washed x3 in saline and resuspended in 0.2cc of normal saline. 15 ml of 1.1% calcium chloride was then added to the resuspension and the islets were incubated again for 10 minutes. Thereafter, the islets were washed in normal saline x2. The result was a somewhat shaggy appearance of the islet surface with some alginate attached, a thin layer of cross-linked alginate surrounding each islet. Thereafter, these pretreated islets were processed into either "single-wall" or "double-wall" microcapsules.

Microencapsulation

Our microencapsulation method was adapted from the previously published methods of Reach, et al. (20, 21). A complete description of our method has been published on several occasions (2, 10, 23, 45, 55).

Briefly, isolated islets were suspended in 1.85%–2.0% sodium alginate in saline and droplets containing islets in alginate were produced by extrusion through a 22 gauge air-jet needle. Droplets of alginate containing islets flowed into a beaker containing 1.1% calcium chloride in saline. The negatively charged alginate droplets bound calcium and formed a calcium alginate gel. Gelled droplets were decanted and subsequently incubated in calcium for 10 minutes.

Thereafter, sequential washes with more dilute calcium chloride solutions were followed by a final wash in saline, after which 0.5 mg/ml poly-1-lysine was added and a subsequent incubation of 6 minutes allowed for the positively charged poly-1-lysine to displace calcium ions and bind negatively charged alginate, producing a polyelectrolyte membrane. We used poly-1-lysine of 18–25,000 molecular weight. Following the poly-1-lysine incubation, microcapsules were washed in 0.1% CHES and a final 0.185%–0.2% solution of sodium alginate was added, forming a thin outer coating of sodium alginate. Finally, capsulates were incubated in 55 mM sodium citrate, solubizing any calcium alginate which had not reacted with poly-1-lysine.

Figure 9A:
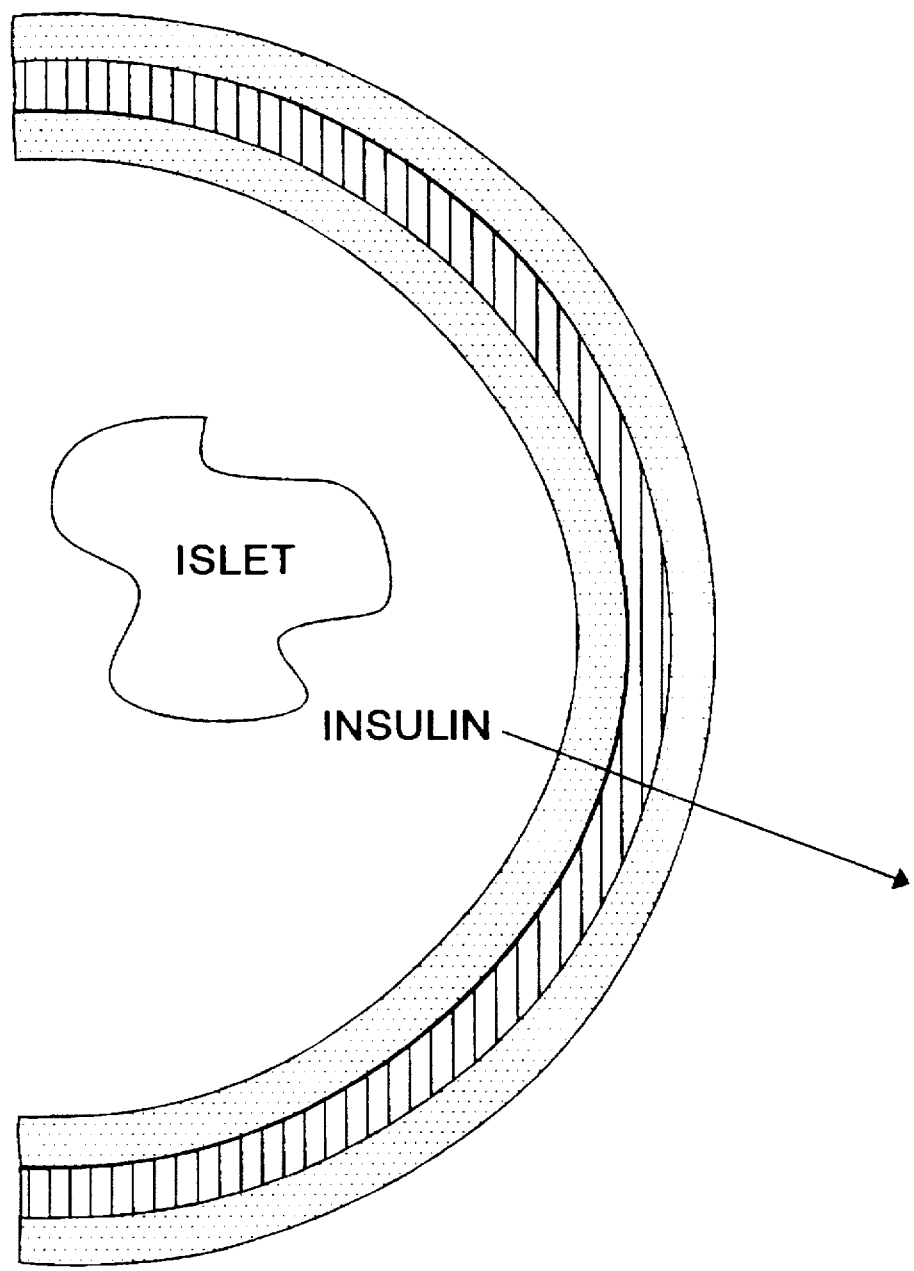
FIGS. 9A and 9B: Schematics of "single-wall" (FIG. 9A) and "double-wall" (FIG. 9B) microcapsules. In each representation, alginate layers are depicted as shaded and poly-1-lysine layers are depicted as hatched.
Figure 9B:
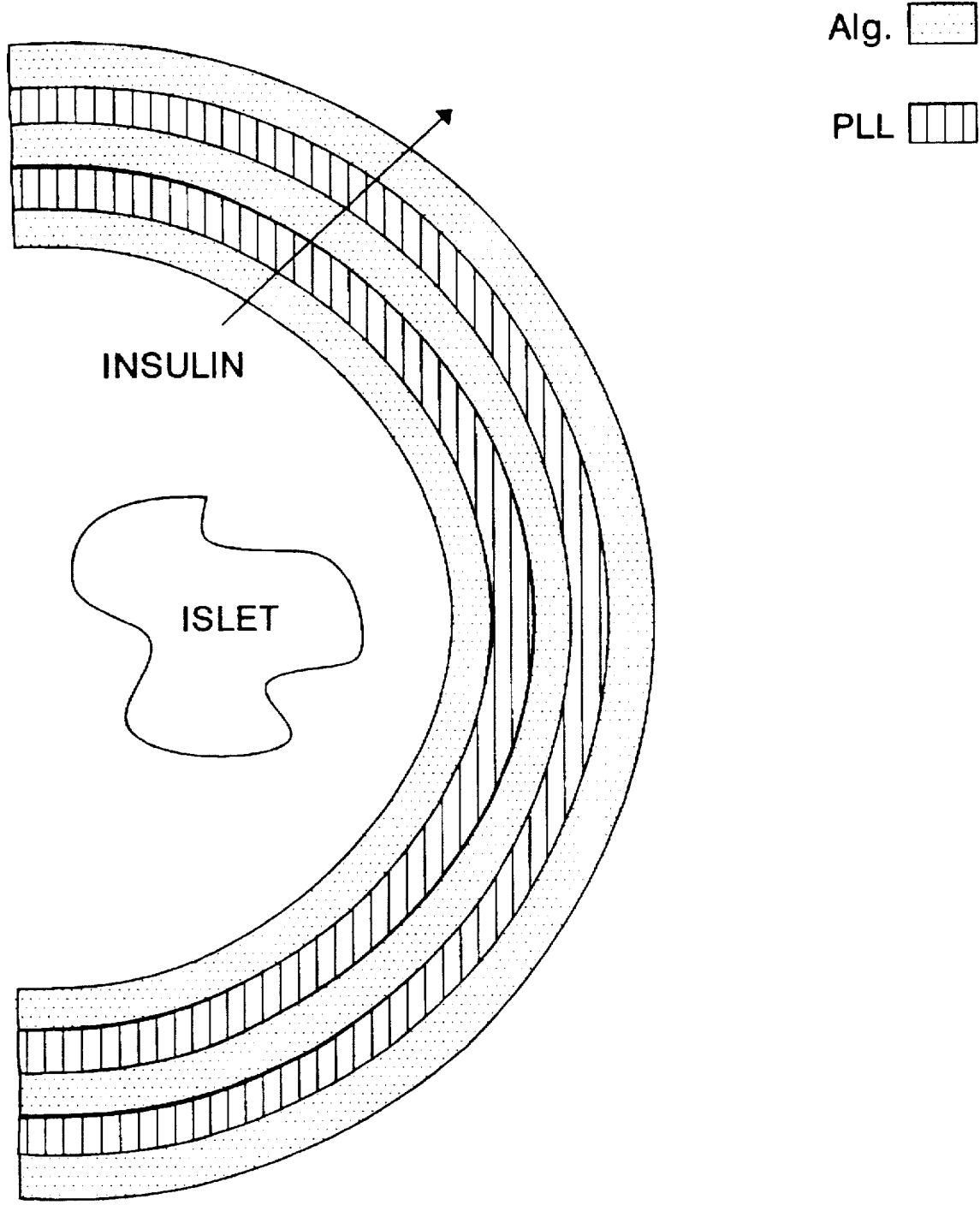

For formation of "double-wall" microcapsules, after completion of the "single-wall" by the method above, but prior to the sodium citrate incubation, additional poly-1-lysine was added and a second incubation of 6 minutes was followed by a subsequent wash in 0.1% CHES followed by an additional reincubation in dilute 0.185%–0.2% sodium alginate, followed by a final sodium citrate incubation. For some of the "double-wall" microcapsules, isolated islets were initially suspended in a solution of 2.0% sodium alginate in saline, rather than 1.85% sodium alginate in saline. (See also FIGS. 1, 9A and 9B).

Results

Results are shown in Table 1 and in Table 2:

TABLE 1

| Islet Donor | Mouse Recipient | Site | Capsule Type & Mouse Treatment | (N) | Graft Survival (Days) | X ± SEM | Comments |
|---|---|---|---|---|---|---|---|
| RAT | C57 | C | SW, 1.85% | 5 | 30, >200 X4 | 100. | NO REACTION |
| RAT | NOD | C | SW, 1.85% | 10 | 6,7,8,8,13,13,16,17,17,21 | 12.6 ± 1.2 | 4⁺ CELLULAR REACTION |
| RAT | NOD | C | DW, 1.85% | 9 | 9,11,15,16,16,19,21,31,34 | 19.1 ± 2.89ψψ | 4⁺ CELLULAR REACTION |
| RAT | NOD | S | NONE | 5 | 3,5,5,5,6 | 4.8 ± 0.5 | ISLETS NECROTIC |
| RAT | B10. | C | DW, 1.85% | 5 | 95,99,126,161*,180* | 132.2 ± 16.8ψ▲§ | NO CELLULAR REACTION |
| RAT | B10. | S | NONE | 5 | 9,9,10,11,12 | 10.2 ± 0.6ψ | ISLETS NECROTIC |
| RAT | NOD | C | DW, 2.0% | 5 | 34,34,84,142,136 | 86 ± 23.5## | NO REACTION (excludes IgG) |
| RAT | NOD | C | PT, DW, 2.0% | 7 | 18,21,81,100,115,165*, >263 | 109 ± 32.3** | NO REACTION (excludes IgG) |
| RABBIT | NOD | C | DW, 2.0% | 7 | 12,15*,17, >18,18,20,28 | 18.2 ± 1.89 | 3⁺4⁺ REACTION (excludes IgG) |
| RABBIT | NOD | C | PT, DW, 2.0% | 4 | 15*,35,41,32 | 30.75 ± 5.57*** | 3⁺–4⁺ REACTION (excludes IgG) |

C = intraperitoneal microcapsular
S = intrasplenic, not encapsulated

TABLE 1-continued

| Islet Donor | Mouse Recipient | Site | Capsule Type & Mouse Treatment | (N) | Graft Survival (Days) | X ± SEM | Comments |
|---|---|---|---|---|---|---|---|

* = sacrificed
@ = p < .001 vs. intrasplenic contr.
ψ = p < .001 vs. NODs
+ = p = NS vs. B10.
▲ = p < .0001 vs. intrasplenic contr.
§ = p < .0001 vs. B10. N − 2⁶³
SW, 1.85% = "single-wall", 1.85% alginate
Dw, 1.85% = "double-wall", 1.85% alginate
DW, 2.0% = "double-wall", 2.0% alginate
PT, DW, 2.0% = islet pretreatment, "double-wall", 2.0% alginate
Graft survival = # days, blood glucose <250. mg/dl.
ψψ = p < 0.1 vs. SW, 1.85%
** = p = NS vs. DW, 2.0%
*** = p < .02 vs. DW, 2.0%
## = p < .002 vs. DW, 1.85%

TABLE 2

Islet Iso-, Allo-, and Xenografts in Diabetic NOD Mice

| Group Islet Donor-Recip. | Site | Capsule Type | Mouse Rx | (N) | Graft Survival (Days) (BG < 250. mg/dl) X ± SEM | Reaction (0-4+) |
|---|---|---|---|---|---|---|
| 1) RAT-NOD | I.P. | SW, 1.85 | (—) | 10 | 13 ± 1Ω | 4⁺ |
| 2) RAT-NOD | I.P. | DW, 1.85 | (—) | 9 | 19 ± 30* | 4⁺ |
| 3) RAT-NOD | S | (—) | (—) | 5 | 5 ± 0.5 | 4⁺ |
| 4) RAT-B10 | I.P. | DW, 1.85 | (—) | 5 | 132 ± 17+ | 0 |
| 5) RAT-B10 | S | (—) | (—) | 5 | 10 ± 0.6+ | 4⁺ |
| 6) PIG-NOD | I.P. | DW, 1.85 | (—) | 2 | 6,9 | 4⁺ |
| 7) RAT-NOD | I.P. | DW, 2.0 | (—) | 5 | 86 ± 24## | 1⁺(#) |
| 8) RAT-NOD | I.P. | DW, 2.0 | Rat-Spleen Cell | 1 | 10 | 4⁺ |
| 9) RAT-NOD | I.P. | PT, DW, 2.0 | (—) | 7 | 126 ± 47## | 1⁺(#) |
| 10) RAT-NOD | S | (—) | CTLA4 | 5 | 6 ± 0.2 | 4⁺ |
| 11) RABBIT-NOD | I.P. | DW, 2.0 | (—) | 5 | 19 ± 3 | 4⁺(#) |
| 12) RABBIT-NOD | I.P. | DW, 2.0 | CTLA4 | 7 | 80 ± 26@ | 0(#) |
| 13) RABBIT-NOD | R | (—) | CTLA4 | 2 | 5,6 | 4⁺ |
| 14) RABBIT-NOD | I.P. | PT, DW, 2.0 | (—) | 4 | 31 ± 6@ | 4⁺(#) |
| 15) RABBIT-NOD | I.P. | DW, 2.0 | 10-2.16 | 5 | 15 ± 1 | 4⁺(#) |
| 16) RABBIT-NOD | I.P. | DW, 2.0 | 53-6.7 | 4 | 22 ± 6 | 3⁺(#) |
| 17) RABBIT-NOD | I.P. | DW, 2.0 | CyA | 4 | 22 ± 3Σ | 4⁺(#) |
| 18) RABBIT-NOD | I.P. | DW, 2.0 | 14-4-4 | 4 | 55 ± 29Σ | 3⁺(#) |
| 19) CALF-NOD | I.P. | DW, 2.0 | (—) | 1 | 24 | 3⁺(#) |
| 20) DOG-NOD | I.P. | DW, 2.0 | (—) | 3 | 14 ± 4 | 3⁺(#) |
| 21) BALB/C-NOD | I.P. | DW, 2.0 | (—) | 4 | 52 ± 36 | 0-1⁺(#) |
| 22) NOD-NOD | I.P. | DW, 2.0 | (—) | 3 | 48 ± 7 | 0-1⁺(#) |
| 23) RABBIT-NOD-Scid | I.P. | DW, 2.0 | (—) | 1 | 10⁺ | |
| 24) RABBIT-NOD-Scid | S | (—) | (—) | 1 | 10⁺ | |
| 25) Human-NOD | I.P. | DW, 2.0 | (—) | 1 | 6 | 3⁺(#) |

R = renal capsule (islets not encapsulated)
I.P. = intraperitoneal encapsulated islets
S = intrasplenic (islets not encapsulated)
Ω = p < .001 vs. intrasplenic contr.
+ = P < .001 vs. NODs
SW, 1.85 = "single-wall", 1.85% alginate
DW, 1.85 = "double-wall", 1.85% alginate
DW, 2.0 = "double-wall", 2.0% alginate
PT, DW, 2.0 = Islet pretreatment, "double-wall", 2% alginate
CTLA4Ig = 200. mcg, i.p., day 0, then Q.O.D.
10.2.16 = 100. mcg, i.p., day-5, ⁺2, then weekly
14.4.4 = 100. mcg, i.p., day-5, ⁺2, then weekly
53.6.7 = 100. mcg, i.p., day-5, ⁺2, then weekly
Cyclosporine = 30. mg/kg, s.c., day-1, then daily
* = p < .01 vs. SW, 1.85%
Σ = p = NS vs. DW, 2.0%
@ = p < .02 vs. DW, 2.0%
# = excludes IgG
## = p < .002 vs. DW, 1.85%

Discussion

Both "single-" and "double-wall" microcapsules were biocompatible in prediabetic NOD mice for greater than 6 months. Occasional inflammatory reactions were present around broken microcapsules, but no reaction was present around intact microcapsules. Seventy-five percent of empty "single-wall" microcapsules were recovered after 6 months (Means of 2 separate experiments, 5 NODs per experiment). For "double-wall" microcapsules, 78 and 81% (Means of 2 separate experiments, 5 NODs each) were recovered after 6 months. "Single-wall" microcapsules were approximately 700–800 microns in diameter and somewhat irregular in contour when recovered, while "double-wall" microcapsules were smaller, approximately 500 microns in diameter, and had visibly thicker, intact membranes (refer to reference 55). Furthermore, rat islets encapsulated with the "double-wall" technique and implanted in NOD mice functioned for significantly longer periods of time than did identical islets encapsulated with a "single-wall" technique (19.1±2.8 days versus 12.6±1.2 days) (Table 1). This "double-wall" technique has been patented (U.S. Pat. No. 5,227,298). Unfortunately, at the time of eventual rejection, a NOD mouse host cellular response was present surrounding rejected "double-wall" microcapsules in a similar fashion to that noted with "single-wall" microcapsules.

Although the improvement in islet xenograft survival in NODs receiving "double" versus "single-wall" encapsulated islets was modest, it was statistically significant. Both "single" and "double-wall" microcapsules dramatically reduced one-way mixed lymphocyte reactivity (23). However, IgG entered both "single" and "double-wall" microcapsules while IgM was excluded (10, 12, 45).

This finding was quite unexpected, since studies by Goosen, King, Halle, et al., and Darquy all had suggested exclusion of IgG by conventional microcapsules produced, as we had done, with poly-1-lysine of MW 17–25K (20, 24, 71, 76).

Since, according to the literature, the poly-1-lysine was optimal (for a permeability<IgG) (<150,000 MW), we chose to reassess the concentration of the other essential reagent, alginate. We tested the effects of increasing alginate concentration from 1.85% to 2.0% and found that this simple, technical alteration yielded poly-1-lysine alginate microcapsules which excluded IgG, and encapsulated rat islet survival increased from 19.1±2.8 days to 86±23.5 days (Table 1).

When grafts with the "double-wall" 2% technique eventually failed, there was evidence of capsule breakage, with reaction to broken capsules and no reaction to intact capsules. In addition, histological evaluations and phase contrast microscopic evaluations of encapsulated islets with both the "single" and "double-wall" technique revealed that 30–50% of capsules had at least one islet embedded in the microcapsule wall, causing some deformity of the wall at that site.

Thus, we confirmed the findings of deVos (77) as well as the previous reports by Chang, et al., (27, 69, 70) who had found similar incorporation of islets and single hepatocytes within the wall of poly-1-lysine alginate microcapsules. It is of interest that several other investigators have published examples of their laboratory's encapsulated islets, not noting the entrapment of islets within the microcapsule wall (6, 21, 24). Chang subsequently patented and published a technique of entrapping initially prepared small calcium alginate beads containing cells within much larger microcapsules, which thereby prevented incorporation of cells within the larger second microcapsule. (See FIG. 1).

We attempted to apply this technique to islet encapsulation and found that these "macrocapsules" were fragile and quite large, measuring approximately 1500–2000 microns. Preliminary studies with rat islets in large microcapsules made with the Chang technique and implanted into either B10 or NOD mice failed, and histologic evaluations revealed that the capsules had disrupted within 2–3 days in vivo. Therefore, we discarded the Chang method and sought additional maneuvers which might prevent incorporation of cells within the wall of microcapsules.

We reinterpreted our findings with the "double-wall" technique, and postulated that the extra layer of poly-1-lysine alginate might have added some thickness and durability to the "single-wall" microcapsule by providing an additional covering over islets which were initially incorporated into the "single-wall" membrane. This interpretation was also consistent with eventual attrition of both "double" and "single-wall" microcapsules, since they had a similar inherent defect in the structure of the capsule wall in a high percentage of capsules (30–50% in our experience).

deVos, et al. (77), had suggested that the number of islets protruding or incorporated into the capsule wall was minimal when capsules were 800 micron in size, with larger numbers of protruding islets observed with both larger and smaller capsule diameters. They also observed less protrusion with a high guloronic acid-content alginate (3% Manugel, Kelco International).

Initially unaware of their report, we chose a different direction. We believed that preincubation of islets in dilute alginate prior to initiation of the encapsulation procedure might prevent their incorporation into the capsule wall and discovered the pretreatment method of the subject invention described herein.

Figure 5:
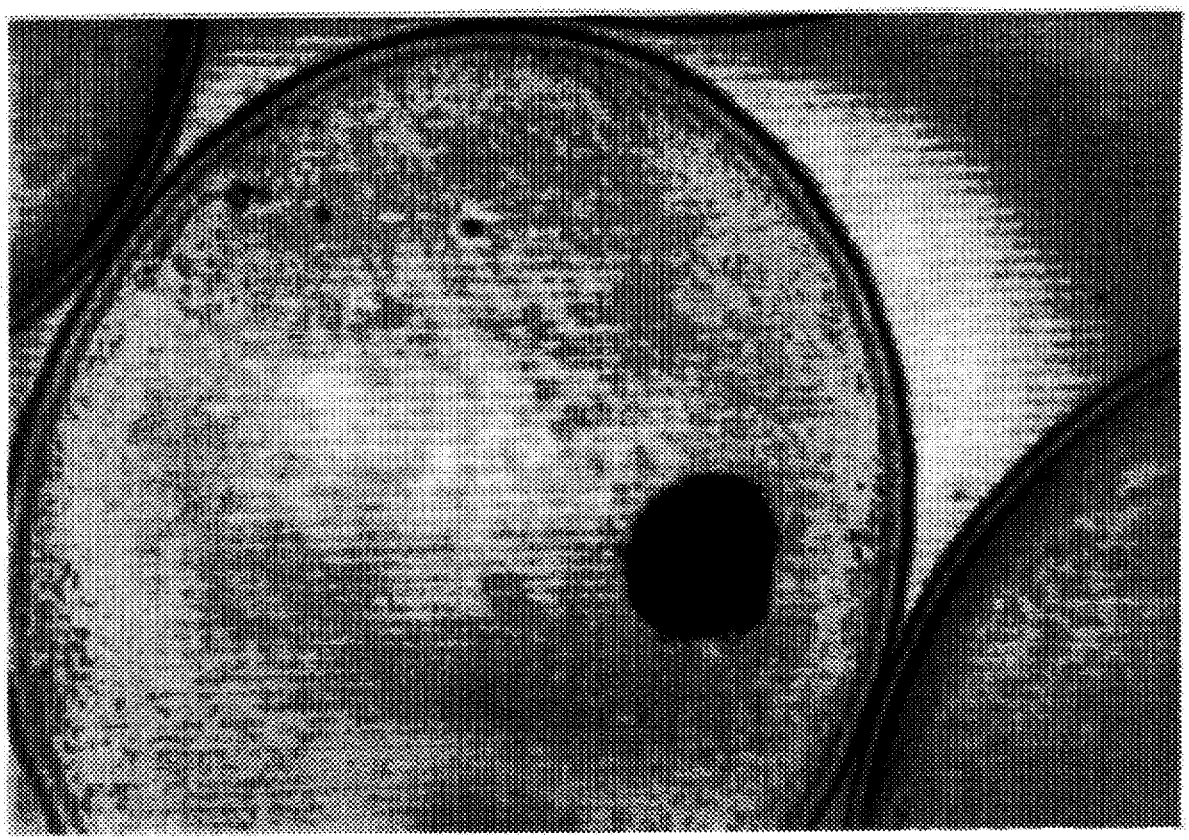
FIG. 5: Islet within microcapsule, not embedded in membrane; new pretreatment method; confocal microscopy.
Figure 6:
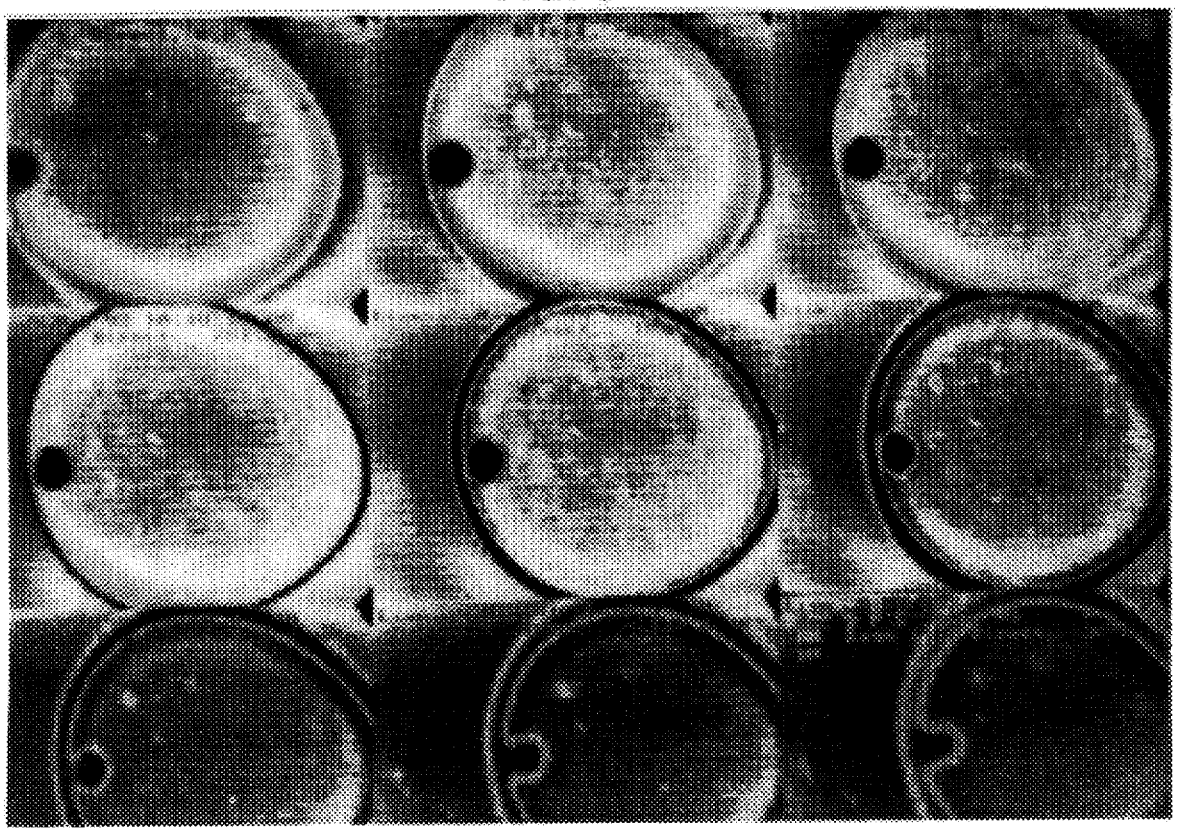
FIG. 6: Same as FIG. 5; note in center image, that when membrane is in focus, islet is within microcapsule, and not embedded in membrane.
Figure 7A:
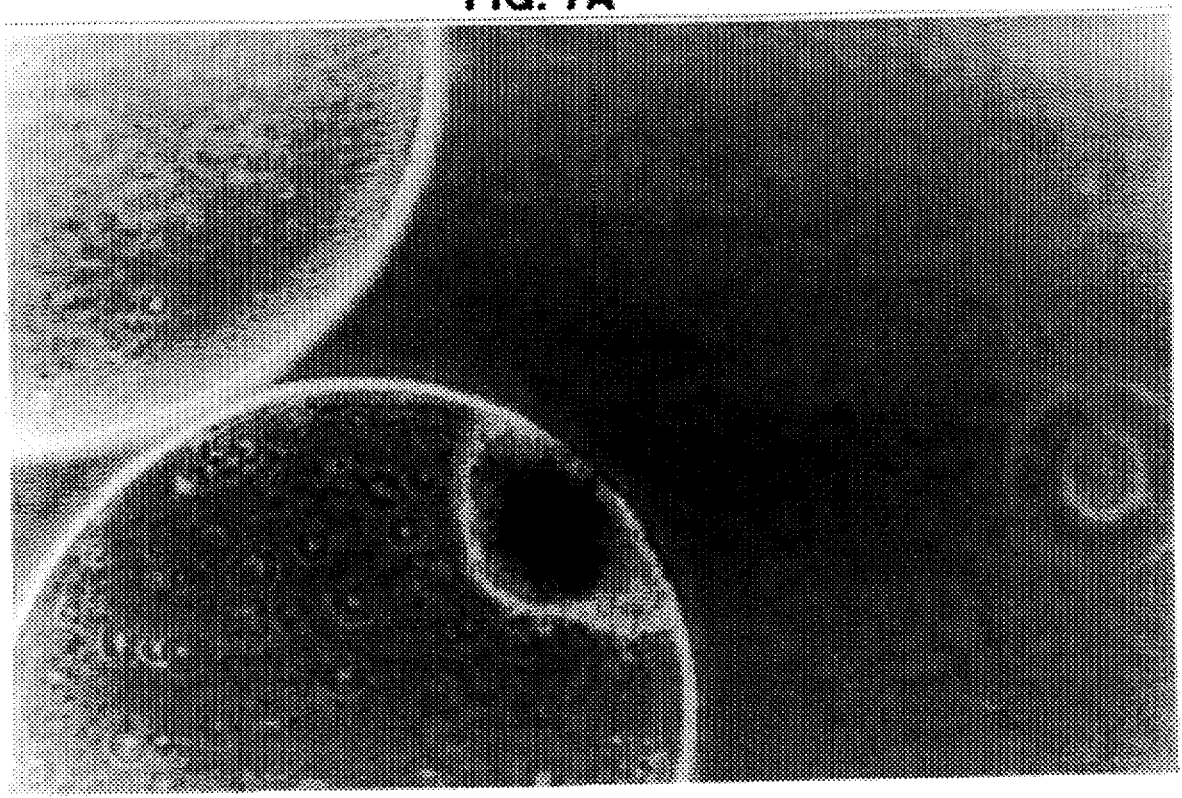
FIGS. 7A and 7B.
Figure 7B:
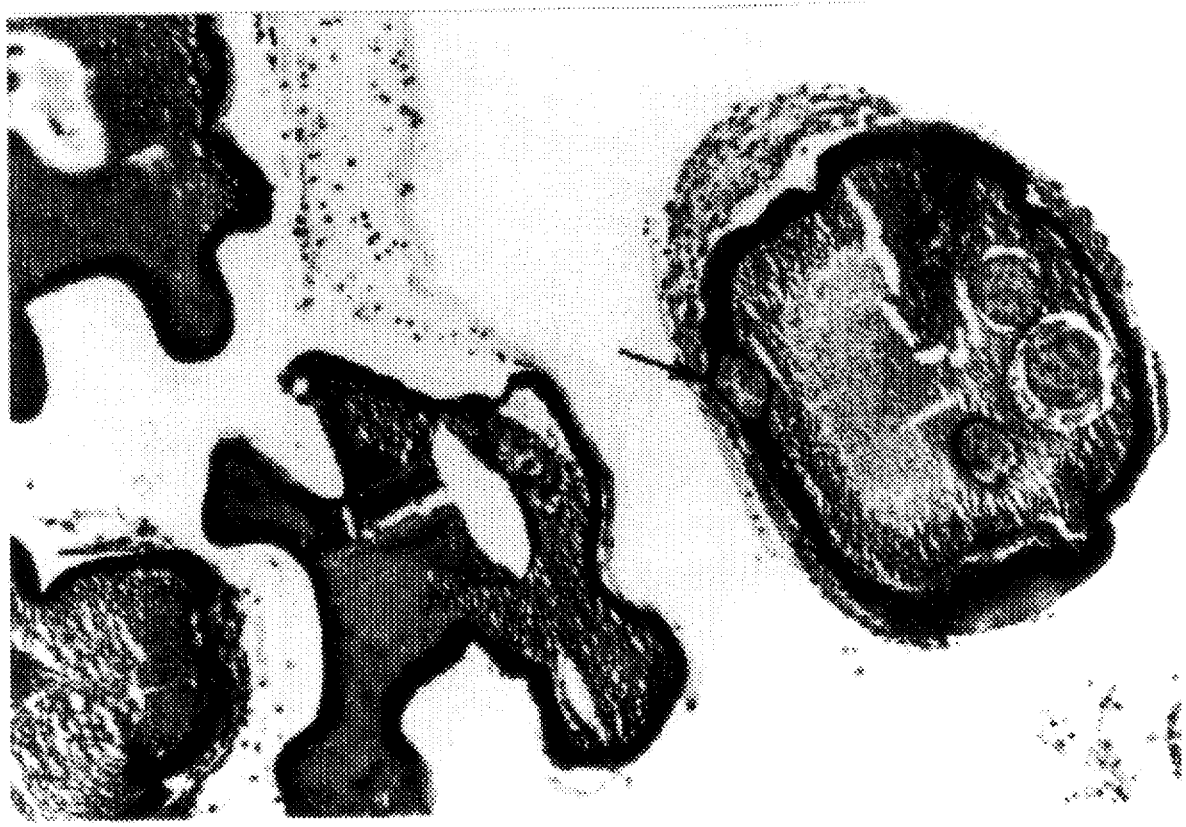
Figure 8:
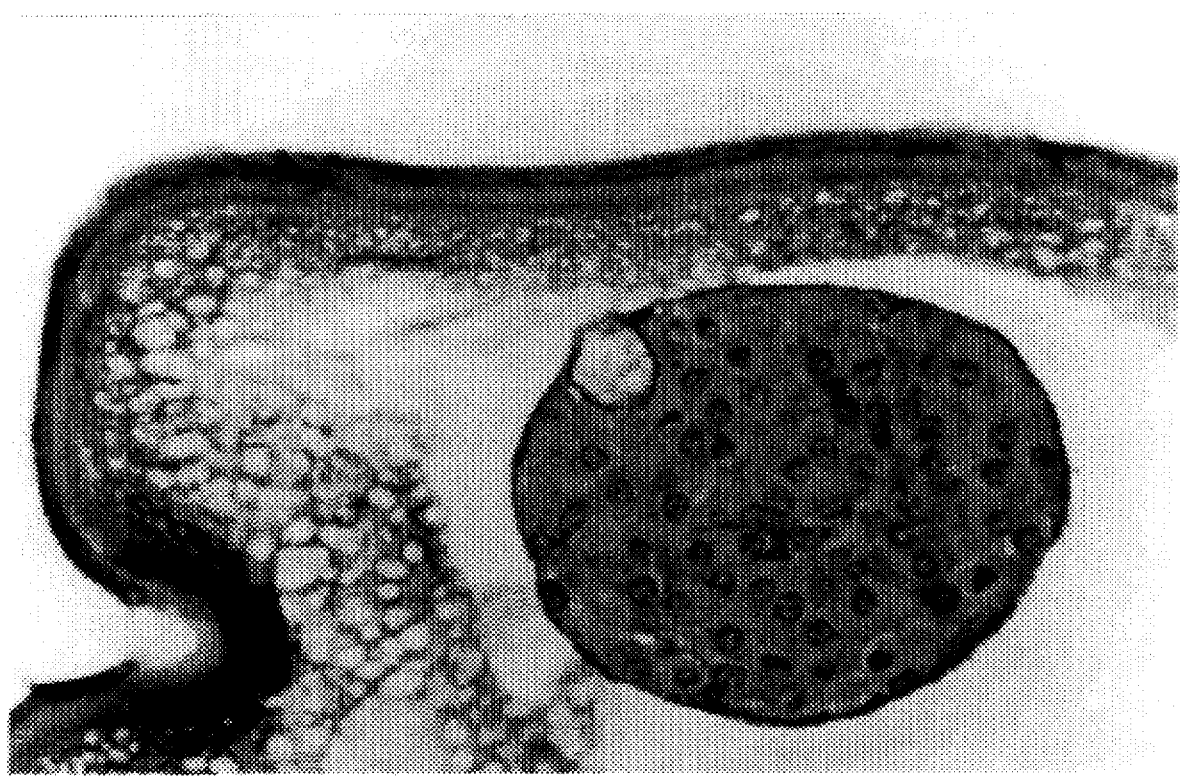
FIG. 8: Biopsy of functioning rat islets in NOD, day 95; "pretreatment (PT)" plus "double-wall", 2.0% alginate. Note islet is free of capsule wall.

Using the pretreatment method of the subject invention, we noted by confocal and phase microscopy that less than 5% of capsules contained an islet embedded in the capsule wall (FIG. 5, FIG. 6, and FIG. 8). To date, we have observed an increase in rat-to-NOD islet graft survival with the pretreatment technique, although there is some variability in graft functional survival (Table 1; Table 2). (See FIG. 8).

We have assessed this technique with an additional islet donor source, the rabbit, and have found two interesting results. First, the "double-wall" 2% alginate technique is much less effective in protecting rabbit islets in NODs than in protecting rat islets in NODs (18.2±1.9 days for rabbit-to-NOD versus 86±23.5 days for rat-to-NOD) (Table 1). On the other hand, pretreatment of rabbit islets followed by "double-wall" 2% encapsulation has resulted in statistically significant prolonged graft survival of rabbit-to-NOD islets when compared to "double-wall" 2.0% technique without pretreatment (30.75±5.6 vs. 18.2±1.9 days) (Table 1).

Most reports of islet xenografts studied concordant rodent donor-recipient combinations, usually rat-to-mouse. We postulated that comparative studies of larger animal islet xenografts into NOD mice would be informative, and potentially more clinically relevant. We chose to compare human, canine, porcine, bovine, rat and mouse islet function in NODs. Human and canine islets were provided (by overnight air transport) by Drs. Ricordi, Rilo and Rajotte. Porcine islets were isolated by the method of Ricordi (86, 10). Newborn bovine islets were isolated by the method of Giannarelli (87), (Mean=25,000 islets/pancreas; N=3) (glucose responsive in vivo in NOD). Rabbit islets were isolated by a method similar to the technique of Vos (88) with a yield of 3,246±1571 islets per pancreas (Mean±S.D.) (N=20).

We have found that there is an apparent hierarchy of encapsulated islet survival in NODs: Rat-NOD=86±23 days;

Balb/C-NOD=51±35 days; rabbit-NOD=18.2±7 days; calf-NOD=21 days (N=1); dog-NOD=14±4 days and pig-NOD=6 and 9 days (N=2). Human=6 days (N=1) (See Table 2). At the time of xenograft rejection, biopsies of microcapsules revealed an intense NOD pericapsular cellular response. These results suggest that different donor-specific antigens may be released, and/or that different mechanisms of antigen presentation and/or effector responses may be involved. Encapsulated islets, from prediabetic NOD donors, isografted to diabetic NOD recipients, are rejected in 48±7 days (Table 2). Biopsies have revealed minimal adherent pericapsular cell response, and nonviable islets within intact capsules. Increased numbers of free peritoneal cell are present, but have not yet been characterized. Thus, isograft rejection differs from xeno- and allo-graft rejection in this model.

Figure 10:
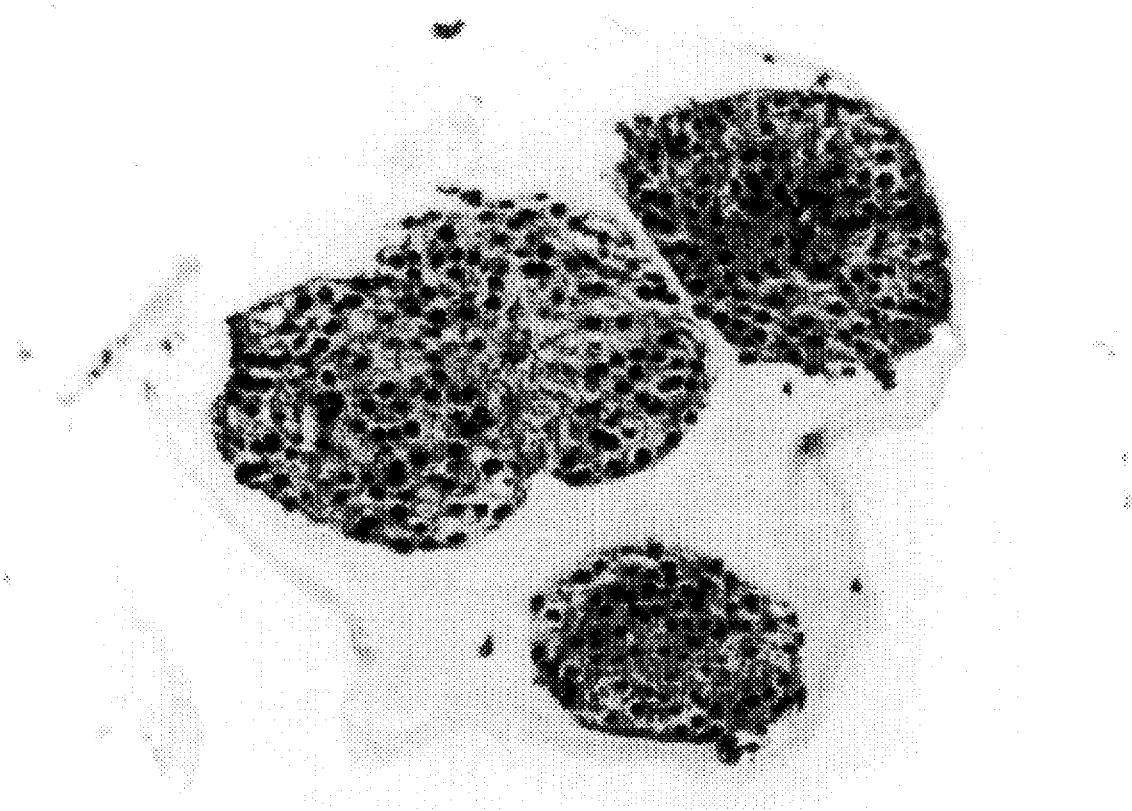
FIG. 10: Encapsulated human parathyroid cells, in culture. H and E histology.

One approach to identification of relevant donor antigens released from microcapsules is encapsulation and transplantation (to NODs) of cells other than islets. One such tissue source is the parathyroid. We have found that human parathyroid cells form "organoids" in culture, which facilitates their encapsulation. (See FIG. 10).

This data shows that donor islet pretreatment as described and claimed is an improvement over standard methods of containing islets within microcapsules. The data also reveal differences in survival of encapsulated discordant (unrelated) versus concordant islet xenografts in NODS.

References

1. Barker C., Naji A.: Perspectives and islet transplantation for diabetes-cures or curiosities?. NEJM 1992;327:1861–8.
2. Weber C., Zabinski S., Koschitzky T., Rajotte R., Wicker L., D'Agati V., Peterson L., Norton J., Reemtsma K.: The role of CD4+ helper T cells in destruction of microencapsulated islet xenografts if NOD mice. Transplantation 1990;49:396–404.
3. Weber C., Zabinski S., Koschitzky T., Wicker L., Rajotte R., Peterson L., D'Agati V., Reemtsma K.: Microencapsulated dog and rat islet xenografts into streptozotocin-diabetic and NOD mice. Horm Metab Res 1990;35:219–26.
4. Mandel T., Koulmanda M., Loudovaris T., Bacelj A.: Islet grafts in NOD mice: A comparison of iso-, allo- and pig xenografts. Transplant proceedings 1989;21:3813–4.
5. Lenschow D., Zeng Y., Thistlethwaite J., Montag A., Brady W., Gibon M., Linsley P., Bluestone J.: Long-term survival of xenogeneic pancreatic islet grafts induced by CTLA4lg. Science 1992;257:789–95.
6. Lum Z., Tai L., Krestow M., Norton J., Vacek L., Sun A.: Prolonged reversal of diabetic state in NOD mice by xenografts of microencapsulated rat islets. Diabetes 1991;40:1511–6.
7. Colton C., Avgoustiniatos E.: Bioengineering in development of the hybrid artificial pancreas. J Biochem Eng 1991;113:152–70.
8. Kowalski L., Falqui L., Lacy P., Scharp D.: Production of marked prolongation of survival of canine islet xenografts in mice by antilymphocyte sera and L3T4 antibody. Transplantation 1991;52:1094–7.
9. Lacy P., Hegre O., Gerasimidi-Vazeou A., Gentile F.: Dionne K.: Maintenance of normoglycemia in diabetic mice by subcutaneous xenografts of encapsulated islets. Science 1991;254:1782–4.
10. Weber C., Costanzo M., Zabinski S., Krekun S., Koschitzky T., D'Agati V., Wicker L., Rajotte R., Reemtsma K., Xenografts of microencapsulated rat, canine, porcine, and human islets into streptozotocin (SZN)—and spontaneously diabetic NOD mice. In: Ricordi C., (Eds). *Pancreatic Islet Transplantation*, R. G. Landes, Austin, 1992:177–90 (appended).
11. Weber C. Krekun S., Koschitzky S., Zabinski S., D'Agati V., Hardy M., Reemtsma K.: Prolonged functional survival of rat-to-NOD mouse islet xenografts by ultraviolet-B (UV-B) irradiation plus microencapsulation of donor islets. Transplantation Proceedings 1991;23:764–6.
12. Weber C., D'Agati V., Ward L., Costanzo M., Rajotte R., Reemtsma K.: Humoral reaction to microencapsulated rat, canine, porcine islet xenografts in spontaneously diabetic NOD mice. Transplantation Proceedings 1993;25:462–3.
13. Platt J., Back F. : The barrier to xenotransplantation. Transplantation 1991;52:937–47.
14. Hasan R., Van den Bogaerde J., Wallwork J., White D.: Evidence that long-term survival of concordant xenografts is achieved by inhibition of antispecies antibody production. Transplantation 1992;54:408–13.
15. Moses R. Winn H., Auchincloss H.: Evidence that multiple defects in cell-surface molecule interactions across species differences are responsible for diminished xenogeneic T cell responses. Transplantation 1992;54:203–9.
16. Platt J., Lindman B., Geller R., Noreen H., Swanson J., Dalmasso A., Back F.: The role of natural antibodies in the activation of xenogeneic endothelial cells. Transplantation 1991;52:1027–43.
17. Altman J., Houlbert D., Callard P.: Long-term plasma glucose normalization in experimental diabetic rats with microencapsulated implants of benign human insulinomas. Transplantation 1986;52:1037.
18. Crooks C., Douglas J., Broughton R., Sefton M.: Microencapsulation of mammalian cells in a HEMA-MMA copolymer: effects on capsule morphology and permeability. J Biomed Mater Res. 1990;24:1241–62.
19. Sugamore M., Sefton M.: Microencapsulation of pancreatic islets in a water insoluble polyacrylate. ASAIO 1989;35:791–9.
20. Darquy S., Reach G.: Immunoisolation of pancreatic B cells by microencapsulation. Diabetologia 1985;28:776–80.
21. Chicheportiche D., Reach G.: In vitro kinetics of insulin release by microencapsulated rat islets: effect of the size of the microcapsule. Diabetologia 1988;31:54–7.
22. Ricker A., Stockberger S., Halban P., Eisenbarth G., Bonner-Weir S. Hyperimmune response to microencapsulated xenogeneic tissue in non obese diabetic mice. In: Jaworski M., (Eds). *The Immunology of Diabetes Mellitus*, Elsevier, Amsterdam, 1986:193–200.
23. Weber C., Zabinski S., Norton J., Koschitzky T., D'Agati V., Reemtsma K. The future role of microencapsulation in xenotransplantation. In: Hardy M., (Eds). *Xenograft 25*, Elsevier, Amsterdam, 1989:297–308.
24. Halle J., Bourassa S., Leblond F., Chevalier S., Beaudry M., Chapdelaine A., Cousineau S., Saintonge J., Yale J.: Protection of islets of Langerhans from antibodies by microencapsulation with alginate-poly-1-lysine membranes. Transplantation 1993;44:350–4.
25. Fritschy W., Strubbe J., Wolters G., VanSchilfgaarde R.: Glucose tolerance and plasma insulin response to intravenous glucose infusion and test means in rats with microencapsulated islet allografts. Diabetologia 1991;34:542–7.
26. Calafiore R. A method for the large-scale production of microencapsulated islets. Diabetes, Nutr & Metab 1992;5:23–9.

27. Chang T. Hybrid artificial cells: Microencapsulation of living cells. ASAIO journal 1992:128–30.
28. Fritschy W., Van Straaten J., De Vos P., Strubbe J., Wolters G., Van Schilfgaarde R.: The efficacy of intraperitoneal pancreas islet isografts in the reversal of diabetes in rats. Transplantation 1991;52:777–83.
29. Lanza R., Sullivan S., Chick W.: Islet transplantation with immunoisolation. Diabetes 1992;41:1503–10.
30. Horcher A., Zekorn T., Siebers U., Klock G., Schnettler R., Arnold M., Federlin K., Aimmerman U., Bretzel R.: Insulin release from different models of a bioartificial pancreas (microencapsulation versus alginate coating). Transplantation Proc 1992;24:2950–1.
31. Gin H., Cadic C., Baquey C., Dupuy B.: Peritoneal exudates from microencapsulated rat islets of Langerhans xenografted mice presenting characteristics of potentially cytotoxic non-specific inflammation. J of Microencapsulation 1992;9:489–94.
32. Zekorn T., Siebers U., Horcher A., Schnettler R., Zimmermann U., Bretzel R., Federlin K.: Alginate coating of islets of Langerhans: in vitro studies on a new method of microencapsulation of immuno-isolated transplantation. Acta Diabetol 1992;29:41–5.
33. Iwata H., Takagi T., Amemiya H., Shimizu H. Yamashita K., Kobayashi K., Akutsu T.: Agarose for a bioartificial pancreas. J Biomed Mater Res 1992;26:967–77.
34. Levesque L., Brubaker P., Sun A.: Maintenance of long-term secretary function by microencapsulated islets of Langerhans. Endocrinology 1992;130:644–90.
35. Clayton H., London N., Colloby P., Bell P., James R.: The effect of capsule composition on the biocompatibility of alginate-poly-1-lysine capsules. J Microencapsulation 1991;8:211–33.
36. Sun A. Microencapsulation of pancreatic islet cells: a bioartificial endocrine pancreas. Methods enzymol 1988;137:575–80.
37. Weber C., Price J., Costanzo M., Becker A., Stall A.: NOD mouse peritoneal cellular response to poly-1-lysine-alginate microencapsulated rat islets. Transplantation Proceedings 1994;26:1116–9.
38. Weber C., Tanna A., Costanzo M., Price J., Peterson L., Wicker L.: Effects of host genetic background on survival or rat→mouse islet xenografts. Transplantation Proceedings 1994;26:1186–8.
39. Auchincloss H. Xenogeneic transplantation. Transplantation 1988;46:1–20.
40. Ricordi C., Lacy P., Sterbenz K., Davie M.: Low-temperature culture of human islets plus in vivo treatment of L3T4 antibody produces a marked prolongation of islet human-to-mouse xenograft survival. Proc Natl Acad Sci 1987;84:8080–4.
41. Pierson R., Winn H., Russell P., Auchincloss H.: CD-4 positive lymphocytes play a dominant role in murine xenogeneic responses. Transplantation Proceedings 1989;21:519–21.
42. Moses R., Pierson R., Winn H., Auchincloss H.: Xenogeneic proliferation and lymphokine production are dependent on CD4+ helper T cells and self antigen-presenting cells in the mouse. J Exp Med 1990;172:567–75.
43. Wijsman J., Atkinson P., Mazheri R.: Histological and immunopathological analysis of recovered encapsulated allogeneic islets from transplanted diabetic BB/W rats. Transplantation 1992;54:588–92.
44. Clayton H., London N., Bell P., Jams R.: The transplantation of encapsulated islets of Langerhans into the peritoneal cavity of the biobreeding rat. Transplantation 1992;54:558–60.
45. Weber C., Costanzo M., Krekun S., D'Agati V.: Causes of destruction of microencapsulated islet grafts: Characteristics of a 'double-wall' poly-1-lysine-alginate microcapsule. Diabetes, Nutrition and Metabolism 1993;1:167–71.
46. Jarpe A., Hickman M., Anderson J.: Flow cytometric enumeration of mononuclear cell populations infiltrating the islets of Langerhans in prediabetic NOD mice: Development of model of autoimmune insulitis for Type 1 diabetes. Regional Immunology 1990;3:305–17.
47. Mandrup-Poulsen T., Bendtzen K., Nerup J.: Affinity-purified human interleukin-1 is cytotoxic to isolated islets of Langerhans. Diabetologia 1986;29:63–7.
48. Rabinovitch A., Sumoski W., Rajotte R., Warnock G.: Cytotoxic effects of cytokines on human pancreatic islet cells in monolayer culture. J of Clinical Endocrinology and Metabolism 1990;50:391–4.
49. Haskins K., Portas M., Bradley B.: T-lymphocyte clone specific for pancreatic islet antigen. Diabetes 1988;37:1444–8.
50. Haskins K., Portas M., Bergman B., Lafferty K., Bradley B.: Pancreatic islet-specific T-cell clones from nonobese diabetic mice. P N A S 1989;86:8000–4.
51. Haskins K., McDuffie M.: Acceleration of diabetes in young NOD mice with a CD4+ islet-specific T cell clone. Science 1990;249:1433–6.
52. Prins J., Todd J., Rodrigues N., Ghosh S., Hogarth M., Wicker L., Gaffney E., Podolin P., Fishcer P., Sirotina A., Peterson L.: Linkage on Chromosome 3 of autoimmune diabetes and defective Fc receptor for IgG in NOD mice. Science 1993;260:695.
53. Lehuen H., Bendelac A., Back J., Carnaud C.: The nonobese diabetic mouse model: independent: expression of humoral and cell-mediated autoimmune features. J Immunol 1990;114:2147–51.
54. Supon P., Stecha P., Haskins K.: Anti-islet cell antibodies from NOD mice. Diabetes 1990;39:1366–92.
55. Weber C., Reemtsma K. Microencapsulation in small animals-II: Xenografts. In: Lanza R., Chick W.: (Eds). *Pancreatic islet transplantation series: Vol III: Immunoisolation of pancreatic islets*, R. Landes, Austin, 1994:59–79.
56. Gill R., Coulombe M.: Rejection of pancreatic islet xenografts does not require CD8+ T-lymphocytes. Transplantation Proceedings 1992;24:2877–8.
57. Loudovaris T., Charlton B., Mandel T.: The role of T cells in the destruction of xenografts within cell-impermeable membranes. Transplantation Proceedings 1992;24:2938.
58. Thai N., Wang S., Valdivia L., Celli S., Reilly M., Demetris A., Simmons R., Stazl T., Fung J.: Cytokine messenger RNA profiles in hamster-to-rat liver xenografts. Transplantation Proceedings 1993;25:444–5.
59. O'Connell P., Pacheoco-Silva A., Nickerson P., Muggia R., Bastos M., Kelley V., Strom T.: Unmodified pancreatic islet allograft rejection results in preferential expression of certain T cell activation transcripts. J Immunol 1993;150:1093–104.
60. Akita K., Ogawa M., Mandel T.: Effect: of FK506 and anti-CD4 therapy on fetal pig pancreas xenografts and host lymphoid cells in NOD/Lt, CBA, and BALB/c mice. Cell Transplantation 1994;3:61–73.
61. Maki T., Lodge P., Carretta M., Ohzato H., Borland K., Sullivan S., Staruk J., Muller T., Solomon B., Chick W., Monaco A.: Treatment of severe diabetes mellitus for more than one year using a vascularized hybrid artificial pancreas. Transplantation 1993;55:713–8.

62. Desai N., Bassiri H., Odorico J., Koller B., Smithies O., Naji A., Barker C., Markmann J.: Pancreatic islet allograft and xenograft survival in CD8+ T-lymphocyte-deficient. Transplantation Proceedings 1993;25:961–2.
63. Lipes M., Rosenzweig A., Tan K., Tanigawa G., Seidman J., Eisenbarth G.: T cell receptor specificity and diabetes in nonobese diabetic mice. Science 1993;262:1582–4.
64. Bergman B., Haskins K.: Islet-specific T-cell clones form the NOD mouse respond to B-granule antigen. Diabetes 1994;43:197–203.
65. Nickerson P., Pacheco-Silva A., O'Connell P., Steurer W., Kelly V., Strom T.: Analysis of cytokine transcripts in pancreatic islet cell allografts during rejection and tolerance induction. Transplantation Proceedings 1993;25:984–5.
66. Serreze D., Gaskins H., Leiter E.: Defects in the differentiation and function of antigen presenting cells in NOD/lt. mice. J Imunol 1993;150:2534–43.
67. Atkinson M., Maclaren N.: Islet cell auto antigens in insulin-dependent diabetes. J Clin Invest 1993;92:1608–16.
68. Zekorn T., Klock G., Horcher A., Siebers U., Wohrle M., Kowalski M., Arnold M., Federlin K., Bretzel R., Zimmermann U.: Lymphoid activation by different crude alginates and the effect of purification. Transpl Proc 1992;24:2952–3.
69. Chang T. Artificial cells in immobilization biotechnology. Art Cells & Immob Biotech 1992;20:1121–43.
70. Wong H., Chang T.: The microencapsulation of cells within alginate poly-1-lysine microcapsules prepared with the standard single step drop technique: histologically identified membrane imperfections and the associated graft rejection. Biomat, Art Cells & Immob Biotech 1991;19:675–86.
71. Goosen M., O'Shea G., Gharapetian H., Chou S., Sun A.: Optimization of microencapsulation parameters: Semipermeable microcapsules as a bioartificial pancreas. Biotechnology and Bioengineering 1985;27:146–50.
72. Kaufman D., Clare-Salzler M., Tian J.: Spontaneous loss of T-cell tolerance to glutamic acid decarboxylase in murine insulin-dependent diabetes. Nature 1993;365:69–72.
73. Tisch R., Yang X., Singer S., Liblau R., Fugger L., McDevitt H.: Immune response to glutamic acid decarboxylase correlates with insulitis in non-obese diabetic mice. Nature 1993;366:72–5.
74. Soon-Shiong P., Heintz R. E., Merideth N., Yao Q. X., Yao Z., Zheng T., Murphy M., Moloney M. K., Schmehl M., Harris M., Mendez R., Sandford P. A.: Insulin independence in a type 1 diabetic patient after encapsulated islet transplantation. Lancet 1994;343:950–1.
75. Colton C. K. The engineering of xenogeneic islet transplantation by immunoisolation. Diab Nutr Metab 1992;5:145–9.
76. King G. A., Daugulis A. J., Faulkner P., Gossen M. F. A.: Alginate-polylysine microcapsules of controlled membrane molecular weight cutoff for mammalian cell culture engineering. Biotechnol Progress 1987;3:231–40.
77. deVos B. J., de Haan G. H. J., Wolters R., Van Schilfgaarde R. Islets protruding from alginate-polylsine microcapsules contribute to bio-incompatibility. Cell Trans. 1994;3:238 [abstract]
78. Aomatsu Y., Nakajima Y., Iwata H.: Indefinite graft survival of discordant islet xenografts in the NOD mouse with agarose microencapsulation and 15-deoxyspergualin. Transpl Proc 1994;26:805–6.
79. Takagi T., Iwata H. Kobayashi K., Foka T., Tsuji T., Ito F.: Development of a microcapsule applicable to islet xenotransplantation. Transpl Proc 1994;26:801.
80. Uludag H., Sefton M. V.: Metabolic activity and proliferation of CHO cells in hydroxyethyl methacrylate-methyl methacrylate (HEMA-MMA) microcapsules. Cell Transpl 1993;2:175–82.
81. Scharp D., Swanson C., Olack B., Latta P., Hegre O., Doherty E., Gentile F., Flavin K., Ansara M., Lacy P. Protection of encapsulated human islets implanted without immunosuppression in patients with Type I or Type II diabetes and in nondiabetic control subjects. Diabetes 1994;43:1167–1170.
82. Horcher A., Zekorn T., Siebers U., Klock G., Frank H., Houben R., Bretzel R. G., Zimmerman U., Federlin K.: Transplantation of microencapsulated islets in rats: Evidence for induction of fibrotic overgrowth by islet alloantigens released from microcapsules. Transpl Proc 1994;26:784–6.
83. Soon-Shiong P., Feldman E., Nelson R., Komtebedde J., Smidsrod O., Skuak-Braek G., Espevik T., Heintz R., Lee M.: Successful reversal of spontaneous diabetes in dogs by intraperitoneal microencapsulated islets. Transplantation 1992;54:769–74.
84. Darquy S., Chicheportiche D., Capron F.: Comparative study of microencapsulated rat islets implanted in different diabetic models in mice. Diabetologia 1989;32:479.
85. Gu J., Gottlieb P.: Inducible functions in hybrids of a Lyt-2+BW5147 tranfectant and the 2C CTLine. Immunogenet 1992;36:283.
86. Ricordi C., Finke E., Lacy P.: A method for the mass isolation of islets from the adult pig pancreas. Diabetes 1986;35:649.
87. Giannarelli R., Marchetti P., Villani G., diCarlo A., Cosimi S., Andreozzi M., Cruschelli L., Masieco P., CCoppelli A., Navalesi R.: Preparation of pure, viable porcine and bovine islets by a simple method. Transplantation Proceedings 1994;26:630–631.
88. Jos V., Connolly J., Deardon D., Pearson R., Parrott N., Johnson R.: A simple method for isolation from the rabbit pancreas. Transplantation 1994;58:390–392.
89. Zhou D., Sun Y., Vacek I., Ma P., Sun A. Normalization of diabetes in cynomolgus monkey xenotransplantation of microencapsulated porcine islets. Transp Proc 1994;26:1091–1092.

What is claimed is:

1. A method of containing a core material within microcapsules having a semipermeable wall to prevent the core material from incorporation into the wall of the microcapsules which comprises:

(a) suspending the core material in a solution containing between about 0.2% and about 0.5% of a polysaccharide gum containing acid groups capable of forming a gel to permit the polysaccharide gum to attach to the core material, wherein the solution of polysaccharide gum is physiologically compatible with the core material;

(b) removing the core material from the solution of polysaccharide gum in step (a) and washing the core material in a solution not containing the polysaccharide gum to remove from the core material all but a thin layer of polysaccharide gum attached to the core material;

(c) treating the washed core material having the attached thin layer of polysaccharide gum from step (b) under conditions to cause the polysaccharide gum attached to the core material to gel to form a pretreated core material;

(d) suspending the pretreated core material from step (c) in a solution containing a polysaccharide gum containing acid groups capable of forming a gel, wherein the solution of polysaccharide gum is physiologically compatible with the core material;

(e) forming the suspension from step (d) into droplets of a size sufficient to encapsulate the core material;

(f) treating the droplets from step (e) under conditions to cause the polysaccharide gum to gel to form temporary shape-retaining capsules; and (g) treating the temporary shape-retaining capsules from step (f) under conditions with a polymeric material containing groups that react with and crosslink acid groups of the temporary shape-retaining capsules to cause the formation of a permanent semipermeable membrane around the capsules to form said microcapsules.

2. The method of claim 1, wherein the polysaccharide gum capable of forming the gel is an alkali metal alginate.

3. The method of claim 1, wherein the final concentration of the alkali metal alginate in the first solution in step (a) is about 0.2%.

4. The method of claim 3, wherein treating the washed core material in step (c) comprises contacting the washed core material with a solution comprising multivalent cations.

5. The method of claim 4, wherein the multivalent cations are calcium cations.

6. The method of claim 1, wherein the semipermeable wall of the microcapsules is impermeable to immune factors.

7. The method of claim 1, wherein the polysaccharide gum in step (d) is an alkali metal alginate.

8. The method of claim 7, wherein treating the droplets comprises contacting the droplets with a solution which comprises multivalent cations.

9. The method of claim 8, wherein the multivalent cations are calcium cations.

10. The method of claim 9, wherein the polymeric material is a polyamino acid.

11. The method of claim 1, wherein the resulting microcapsules are further treated with polymeric material containing groups that react with and crosslink acid groups of the microcapsules to form a second permanent semipermeable membrane around the microcapsules, thereby forming double-walled microcapsules.

12. The method of claim 1, wherein the core material comprises viable tissue.

13. The method of claim 12, wherein the viable tissue comprises pancreatic islet tissue.

14. The method of claim 1, wherein the core material comprises viable cells.

15. The method of claim 14, wherein the viable cells comprise pancreatic beta cells.

16. A method of transplanting a core material from a donor to a subject so as to protect the core material from destruction by the subject's immune system which comprises:

(a) using the core material from the donor as the core material in the double-walled microcapsules produced by the method of claim 11; and (b) transplanting into the subject the double-walled microcapsules, thereby transplanting the core material from the donor to the subject.

17. The method of claim 16, wherein the subject is a human being.

18. The method of claim 16, wherein transplanting into the subject is by intraperitoneal injection.

19. The method of claim 16, wherein the donor and the subject are different species.

20. The method of claim 19, wherein the donor and the subject are both mammals.

21. A method of treating a diabetic subject which comprises using an amount of viable pancreatic islet tissue or cells from a donor as the core material in the method of claim 16, wherein the amount of viable pancreatic islet tissue or cells transplanted is an amount effective to treat diabetes in the subject.

22. The method of claim 12, wherein the viable tissue is selected from the group consisting of neuroectodermal tissue, hepatocyte tissue, parathyroid tissue, pituitary tissue and lymphoid tissue.

23. The method of claim 14, wherein the viable cells are selected from the group consisting of adrenal cells, hepatocyte cells, parathyroid cells, pituitary cells and lymphocyte cells.

24. Microcapsules containing core material prepared by the method of claim 1.

25. Double-walled microcapsules containing core material prepared by the method of claim 11.

* * * * *